United States Patent [19]

Shiraishi et al.

[11] Patent Number: 5,354,913
[45] Date of Patent: Oct. 11, 1994

[54] OPTICALLY ACTIVE PHENOL DERIVATIVES AND PREPARATION THEREOF

[75] Inventors: Mitsuru Shiraishi, Amagasaki; Shoji Fukumoto, Kobe, both of Japan

[73] Assignee: Takeda Chemical Industries, Ltd., Osaka, Japan

[21] Appl. No.: 85,166

[22] Filed: Jul. 2, 1993

[30] Foreign Application Priority Data

Jul. 3, 1992 [JP] Japan .................................. 4-177043
Jun. 1, 1993 [JP] Japan .................................. 5-130296

[51] Int. Cl.$^5$ ........................ C07C 39/10; C07C 39/08
[52] U.S. Cl. ...................................... 568/766; 544/171; 546/225; 562/455; 568/717; 568/737; 568/763
[58] Field of Search .............. 568/780, 766, 731, 735, 568/737, 743, 744, 745, 746, 747, 734, 717, 722, 723, 236; 514/236, 237; 562/455, 463; 544/171; 546/225

[56] References Cited

U.S. PATENT DOCUMENTS 2,933,523  4/1960  Greenlee .............................. 568/717
3,058,946  10/1962  Nametz ................................. 568/717
3,471,537  10/1969  Berke .................................. 568/717
5,162,571  11/1991  Shiraishi et al. .................. 514/237.5

FOREIGN PATENT DOCUMENTS 0171251  12/1992  European Pat. Off. .

OTHER PUBLICATIONS

Mitsunobu, Synthesis, 1981, pp. 1–28, Jan. 1981.

*Primary Examiner*—Werren B. Lone
*Attorney, Agent, or Firm*—Wenderoth, Lind & Ponack

[57] ABSTRACT

An optically active tri-substituted methane compound having, as substituents, an aromatic ring group and a phenyl group having hydroxyl group at ortho or para position can be obtained by allowing a phenol compound unsubstituted at the ortho- or/and para-position to react with an optically active secondary carbinol compound having an aromatic ring group at the alpha-position in the presence of tri-substituted phosphine and diazodicarboxylate or diazodicarboxamide. These and other optically active tri-substituted methane compounds are useful as active ingredients for medicines or as intermediate compounds for preparing medicines.

15 Claims, No Drawings

OPTICALLY ACTIVE PHENOL DERIVATIVES AND PREPARATION THEREOF

INDUSTRIAL FIELD OF UTILIZATION

This invention relates to a novel optically active phenol derivatives useful as medicines and intermediates for their synthesis and a novel process for producing thereof. The novel optically active phenol derivatives of the present invention have therapeutic and prophylactic activities against cerebral, cardiac, renal and pulmonary circulatory system diseases, respiratory diseases, allergy, anaphylactic shock, endotoxin shock, inflammation and the like as well as inhibiting activities against vascularization by oncocytes.

There have been advanced synthetic studies of substances for antagonizing the receptor of eicosanoids such as thromboxane $A_2$, prostaglandin $H_2$, prostaglandin $D_2$ and the like involved in arachidonic acid cascade; substances for inhibiting 5-lipoxygenase which is an incipient enzyme for biosynthesis of leukotrienes; substances for eliminating active oxygen or inhibiting formation of active oxygen; and the like. For example, in Japanese Patent Laid Open Publication No. 2-15290, there are disclosed certain benzene derivatives having these activities. However, the compounds shown in the reference are in racemic form.

PRIOR ART

As a method of introducing an alkyl group or an aralkyl group into the ortho-position of a phenol compound, Friedel-Crafts reaction using an acid catalyst (e.g. B. R. Castro, "Organic Reactions" Vol. 29, John Wiley & Sons, Inc. New York, 1983, p. 1) has been known as a conventional one. In this method, a phenol derivative obtained by condensation with α-substituted benzyl alcohol is a racemic compound, as disclosed in, for example, JPA H2(1990)-152940. On the other hand, it has been reported that, in the condensation reaction of a phenol compound with an alcohol by combination of triphenylphosphine and diethyl diazodicarboxylate, namely Mitsunobu reaction, corresponding alkyl arylether can be obtained in a good yield (e.g. O. Mitsunobu, Synthesis, 1981, 1). However, no report disclosing direct introduction of a carbon substituent into the carbon at the 2-position of phenol ring, as in the present invention, has been found.

One object of the present invention is to provide novel optically active phenol derivatives which have active oxygen eliminating activity together with antagonistic activity to the receptor of eicosanoides such as thromboxane $A_2$, prostaglandin $H_2$, prostaglandin $D_2$ and the like or 5-lipoxygenase inhibiting activity and thereby have therapeutic and prophylactic activities against cerebral, cardiac, renal and pulmonary circulatory system diseases, respiratory diseases, allergy, anaphylactic shock, endotoxin shock, inflammation and the like as well as inhibiting activities against vascularization by oncocytes.

The present invention is to provide a novel process for producing optically active phenol derivatives, which comprises introducing a carbon substituent into the 2-position carbon on the phenol ring under mild and convenient means. By way of the present invention, the steric configuration of the substituent at the 2-position carbon on the phenol ring can be controlled.

Means of Solving the Problems

The present invention relates to a process for preparing an optically active tri-substituted methane compound (III) having, as substituents, an aromatic ring group and a phenyl group having a hydroxyl group at the ortho- or para-position, which is characterized by allowing a phenol compound (I) unsubstituted at the ortho- or/and para-position to react with a secondary carbinol compound (II) having an aromatic ring group at the α-position in the presence of tri-substituted phosphine and diazodicarboxylate or diazodicarboxamide, and also relates to an optically active phenol derivative represented by the general formula:

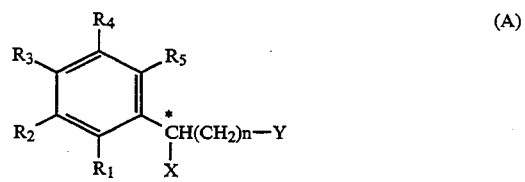

(A)

wherein $R_1$ is an optionally protected hydroxy group; $R_2$ is hydrogen atom, hydroxy group, a lower alkyl group or a lower alkoxy group; $R_3$ is hydrogen atom, hydroxy group, an optionally substituted alkyl group having 1 to 8 carbon atoms, an optionally substituted aralkyl group, a halogen atom, an optionally protected formyl group, an acyl group having 2 to 7 carbon atoms, an optionally esterified or amidated carboxyl group, —CH=CHR_6 group (wherein $R_6$ is a lower alkyl group or a lower acyl group) or —CH=NR_7 (wherein $R_7$ is hydroxy group, a lower alkoxy group, a lower alkenyloxy group or benzhydryloxy group); $R_4$ is an optionally substituted alkyl having 1 to 8 carbon atoms, an optionally substituted aralkyl group, a halogen atom, an optionally protected formyl group, an acyl group having 2 to 7 carbon atoms, an optionally esterified or amidated carboxyl group, —CH=CHR_6 (wherein $R_6$ is as defined above) or —CH=NR_7 (wherein $R_7$ is as defined above); $R_5$ is hydrogen atom or a lower alkyl group; or adjacent two of $R_2$, $R_3$, $R_4$ and $R_5$ may bond to each other to form —(CH_2)_a— group (wherein a is 3 or 4), —CH=CH—CH=CH— group, —(CH_2)_b—CO— group (wherein b is 2 or 3) or —(CH_2)_l—CO—O— group (l is 1 or 2); X is phenyl group optionally substituted with a halogen atom, a lower alkyl group or a lower alkoxy group at the para-position thereof or thienyl group; Y is methyl group, an optionally substituted hydroxymethyl group, an optionally esterified or amidated carboxyl group, cyano group or tetrazolyl group; n is an integer of 3 to 15; and C means an asymmetric carbon atom.

The above-mentioned phenol compound (I) includes any one so long as at least one of the ortho- and para-positions thereof is unsubstituted, and while other positions may be unsubstituted, they may be substituted with various substituents which do not take part in the reaction.

More specifically, the phenol compound (I) can be represented by the general formula given below.

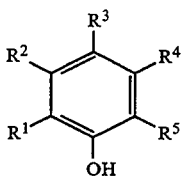

(I-1)

(wherein $R^1$, $R^2$, $R^3$, $R^4$ and $R^5$, independently, stand for a hydrogen atom or a group which does not take part in the reaction, and adjacent two groups of them may be combined to each other to form a ring together with the carbon atom on the benzene ring to which they bond, provided that at least one of $R^3$ and $R^5$ stands for a hydrogen atom).

Examples of the groups of $R^1$ to $R^5$ include a lower alkyl group, a lower alkenyl group, a lower alkoxy group, cycloalkyl group, cycloalkyloxy group, a lower alkylthio group, aralkyl group, aralkyloxy group, aralkylthio group, formyl group, acyl group, acyloxy group, a halogen atom, cyano group, a group represented by the general formula —CH=N—OA (wherein A stands for a lower alkyl group, a lower alkenyl group or an optionally substituted aralkyl group), an esterified or amidated carboxyl group, and, besides, a protected hydroxyl group. Examples of the case where adjacent two of these groups form a ring together with the carbon atom on the benzene ring to which they bond include, as examples of adjacent two of $R^1$ to $R^5$, —(CH$_2$)$_a$— group (a denotes 3 or 4), —CH=CH—CH=CH— group, —(CH$_2$)$_b$—CO— group (b denotes 2 or 3), or —(CH$_2$)$_l$—CO—O— group (l denotes 1 or 2).

Examples of the above-mentioned lower alkyl group include $C_1$–$C_6$ ones such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl. This lower alkyl group may further be substituted with, for example, a $C_1$–$C_4$ alkoxy group (e.g. methoxy, ethoxy, etc.), a protected hydroxyl group (e.g. tetrahydropyranyloxy, tetrahydrofuryloxy, trimethylsilyloxy, t-butylsilyloxy, t-butyldimethylsilyloxy, etc.), an optionally substituted aralkyloxy group (e.g. benzyloxy, diphenylmethyloxy, 4-methoxybenzyloxy, 4-bromobenzyloxy, etc.), a $C_2$–$C_7$ acyloxy group (e.g. acetoxy, propionyloxy, etc.) and an optionally substituted benzoyloxy group (e.g. benzoyloxy, 4-methylbenzoyloxy, 4-methoxybenzoyloxy, 4-bromobenzoyloxy, etc.). Examples of thus-substituted lower alkyl groups include methoxymethyl, methoxyethyl, ethoxymethyl, tetrahydropyranyloxymethyl, tetrahydropyranyloxyethyl, trimethylsilyloxymethyl, trimethylsilyloxyethyl, tertbutyldimethylsilyloxymethyl, tertbutyldimethylsilyloxyethyl, benzyloxymethyl, benzyloxyethyl, diphenylmethyloxymethyl, diphenylmethyloxyethyl, 4-methoxybenzyloxymethyl, 4-methoxybenzyloxyethyl, 4-bromobenzyloxymethyl, 4-bromobenzyloxyethyl, acetoxymethyl, acetoxyethyl, propionyloxymethyl, propionyloxyethyl, benzoyloxymethyl, benzoyloxyethyl, 4-methylbenzoyloxynethyl, 4-methylbenzoyloxyethyl, 4-methoxybenzoyloxymethyl, 4-methoxybenzoyloxyethyl, 4-bromobenzoyloxymethyl, 4-bromobenzoyloxyethyl, among others.

Examples of the lower alkenyl group include $C_2$–$C_6$ ones such as vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl and 5-hexenyl. These groups may optionally be substituted with an acyl group (for example, alkanoyl group such as acetyl, propionyl, butyryl, isobutyryl, valeryl, isovaleryl, pivaloyl, hexanoyl, etc., or cycloalkanecarbonyl such as cyclopentanecarbonyl, cyclohexanecarbonyl, etc.).

Examples of the lower alkoxy group include $C_1$–$C_6$ ones such as methoxy, ethoxy, propoxy, isopropoxy, butoxy, isobutoxy, sec-butoxy, tert-butoxy, pentyloxy, isopentyloxy, neopentyloxy, tert-pentyloxy, 1-ethylpropoxy, hexyloxy, isohexyloxy, 1,1-dimethylbutoxy, 2,2-dimethylbutoxy, 3,3-dimethylbutoxy and 2-ethylbutoxy. These groups may further be substituted. Examples the substituted lower alkoxy group include those in which the substituted lower alkyl moiety is similar to that of the above-mentioned substituted lower alkyl.

Examples of the cycloalkyl group include $C_3$–$C_6$ ones such as cyclopropyl, cyclobutyl, cyclopentyl and cyclohexyl. Examples of the cycloalkyloxy group include $C_3$–$C_6$ ones such as cyclopropyloxy, cyclobutyloxy, cyclopentyloxy and cyclohexyloxy, As the lower alkylthio group, mention is made of ones in which the lower alkyl moiety is the above-mentioned lower alkyl. And, they may be substituted similarly to the case of said lower alkyl.

Examples of the aralkyl group include $C_7$–$C_{13}$ ones such as benzyl, 1-phenylethyl, 2-phenylethyl, 3-phenylpropyl, (1-naphthyl)methyl, (2-naphthyl)methyl and diphenylmethyl. These groups may have substituents at optional positions on the benzene ring. Examples of these substituents include $C_1$–$C_4$ alkyl (e.g. methyl, ethyl, etc.), $C_1$–$C_4$ alkoxy (methoxy, ethoxy etc.), $C_2$–$C_5$ alkoxycarbonyl (e.g. methoxycarbonyl, ethoxycarbonyl, etc.), a halogen atom (e.g. fluorine, chlorine, bromine, etc.).

As the aralkyloxy group and the aralkylthio group, mention is made of those in which the aralkyl moiety is the above-mentioned aralkyl group. And, they may be substituted similarly to the case of aralkyl group.

The above-mentioned forTayl group may optionally be substituted. Examples of thus-substituted formyl group include, besides unsubstituted formyl group, 1,3-dioxolan-2-yl, 1,3-dioxan-2-yl, 1,3-oxathiolan-2-yl, and dialkoxymethyl (carbon number of the alkoxy ranges from 1 to 4).

The acyl group is exemplified by $C_2$–$C_7$ ones including a lower ($C_1$–$C_6$) alkanoyl group such as acetyl, propionyl, butyryl, isobutyryl, valeryl, isovaleryl, pivaloyl, hexanoyl, etc., a cycloalkanecarbonyl group such as cyclopentanecarbonyl group, cyclohexanecarbonyl group, etc.

As the acyloxy group, mention is made of ones in which the acyl moiety is the above-mentioned acyl group.

As the halogen atom, mention is made of, for example, fluorine, chlorine and bromine.

As the lower alkyl group shown by A in the formula —CH=N—OA, mention is made of, for example $C_1$–$C_4$ ones such as methyl, ethyl and propyl, the lower alkenyl group is exemplified by $C_1$–$C_4$ ones such as vinyl and 1-propenyl, and the optionally substituted aralkyl group is exemplified by benzyl, 1-phenylethyl, 2-phenylethyl, 3-phenylpropyl, (1-naphthyl)methyl, (2-naphthyl)methyl, diphenylmethyl, etc. These groups may have substituents at optional positions on the benzene ring. Examples of such substituents include $C_1$–$C_4$ alkyl (e.g. methyl, ethyl, etc.), $C_1$–$C_4$ alkoxy (e.g. methoxy, ethoxy, etc.), $C_2$–$C_5$ alkoxycarbonyl (e.g. methoxycarbonyl, ethoxycarbonyl, etc.) and halogen atoms (fluorine, chlorine, bromine, etc.).

Examples of the esterified carboxyl group include lower alkoxycarbonyl (e.g. $C_2$–$C_5$ ones such as methoxycarbonyl, ethoxycarbonyl and tert-butyloxycarbonyl), aralkyloxycarbonyl (e.g. $C_8$–$C_4$ ones such as benzyloxycarbonyl, 4-methoxybenzyloxycarbonyl, 4-nitrobenzyloxycarbonyl and benzhydryloxycarbonyl) and aryloxycarbonyl (e.g. $C_7$–$C_{10}$ ones such as phenoxycarbonyl, 4-methylphenyloxycarbonyl and 4-methoxyphenyloxycarbonyl).

Examples of the amidated carboxyl group include, besides carbamoyl, aminocarbonyl substituted with $C_1$–$C_4$ alkyl (e.g. methylaminocarbonyl, ethylaminocarbonyl, propylaminocarbonyl, isopropylaminocarbonyl, dimethylaminocarbonyl, diethylaminocarbonyl, etc.), cyclic aminocarbonyl (e.g. morpholinocarbonyl, piperidinocarbonyl, pyrrolidinocarbonyl, thiomorpholinocarbonyl, etc.), aralkylaminocarbonyl [e.g. $C_7$–$C_{13}$ ones such as benzylaminocarbonyl, α-phenethylaminocarbonyl, beta-phenethaminocarbonyl, 1-(α-naphthyl)ethylaminocarbonyl, etc.], phenylaminocarbonyl, substituted phenylaminocarbonyl (e.g. p-methylphenylaminocarbonyl, 4-methoxyphenylaminocarbonyl, 4-chlorophenylaminocarbonyl, 4-bromophenylaminocarbonyl, 4-fluorophenylaminocarbonyl, etc.), diphenylaminocarbonyl, among others.

Examples of the protected hydroxyl group include ones protected with conventional protective group of hydroxyl group, such as methoxymethyloxy, tetrahydropyranyloxy, tetrahydrofuryloxy, trimethylsilyloxy, tert-butyldimethylsilyloxy, 2-(trimethylsilyl)ethoxymethoxy, etc.

As preferable phenol compound (I), mention is made of ones in which the ortho-position is unsubstituted, namely compounds represented by the general formula

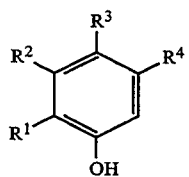

(I-2)

(wherein $R^1$, $R^2$, $R^3$ and $R^4$ independently stand for H or a group which does not take part in the reaction). Among the compounds (1-2), a compound wherein at least two of $R^1$, $R^2$, $R^3$ and $R^4$ are groups other than hydrogen is preferable, and among them, a compound wherein each of $R^1$ and $R^2$ is a group other than hydrogen is the most preferable.

The above-mentioned secondary carbinol compound (II) has an aromatic ring group at its α-position, and is optically active, which is represented by the general formula

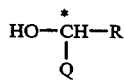

(II-1)

(wherein Q stands for an aromatic ring group and R stands for a groups which does not take part in the reaction. C means an asymmetric carbon atom.).

Examples of the aromatic ring group shown by Q include an aromatic hydrocarbon group and an aromatic heterocyclic group. Examples of the aromatic hydrocarbon group include aryl groups such as phenyl group and naphthyl group (1-naphthyl group, 2-naphthyl group). The aromatic heterocyclic group is the one containing, as a ring-constituting atom, at least one of oxygen atom, sulfur atom and nitrogen atom, which is exemplified by an aromatic monocyclic heterocyclic group such as furyl, thienyl, oxazolyl, thiazolyl, pyridyl, pyridazinyl and pyrimidinyl, and an aromatic condensed heterocyclic group such as benzofuranyl, benzothienyl, benzoxazolyl, benzothiazolyl, quinolyl, isoquinolyl and quinoxalyl. These aromatic hydrocarbon groups and aromatic heterocyclic groups may have optional substituents on the respective rings. Examples of these substituents include halogen atoms (fluorine, chlorine, bromine, etc.), $C_1$–$C_3$ alkyl groups such as methyl, ethyl, etc., $C_1$–$C_3$ alkoxy groups such as methoxy, ethoxy, etc., formayl group, acetyl group, cyano group, phenyl group, benzoyl group, methylenedioxy group, trimethylene group, nitro group, trifluoromethyl group, trifluoromethoxy group, pentafluoroethyl group, etc.

As the group which does not take part in the reaction, shown by R, hydrocarbon groups and aromatic heterocyclic groups are mentioned. As the aromatic heterocyclic groups, mention is made of those shown, by Q described above.

As hydrocarbon groups shown by R, mention is made of aliphatic chain hydrocarbon groups, alicyclic hydrocarbon groups, aromatic hydrocarbon groups and aromatic aliphatic hydrocarbon groups.

As aliphatic chain hydrocarbon groups, mention is made of straight-chain or branched aliphatic hydrocarbon groups, for example, alkyl groups, alkenyl groups, alkynyl groups, etc.

Examples of the alkyl groups include $C_1$–$C_{22}$ ones such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, pentyl, hexyl, heptyl, octyl, nonyl, decyl, undecyl, docosyl, etc. Among them, straight chain ones are preferable.

Examples of alkenyl groups include $C_2$–$C_{22}$ ones such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 3-heptenyl, 3,7-dioctenyl, 3,7-dinonenyl, 3,7-didecenyl, etc. Among the, straight chain ones are preferable.

Examples of alkynyl groups include $C_2$–$C_{22}$ ones such as ethynyl, 1-propinyl, 2-propinyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 3-heptynyl, 4-octynyl, 5-decynyl, 5-undecynyl and 5,10-didodecynyl. Among them, straight chain ones are preferable.

These alkyl, alkenyl and alkynyl groups may optionally have substituents as exemplified by methoxy, acetoxy, benzoyloxy, benzeyloxy having a $C_1$–$C_3$ alkyl group (e.g. methyl, ethyl, etc.), a $C_1$–$C_3$ alkoxy group (e.g. methoxy, ethoxy, etc.) and/or a halogen atom (fluorine, chlorine, bromine, etc.) as substituents [e.g. 4-methylbenzoyloxy, 4-methoxybenzoyloxy, 4-chlorobenzoyloxy, 4-bromobenzoyloxy, etc.], benzyloxy, benzhydryloxy, nitroxy, substituted aminocarbonyloxy (e.g. methylaminocarbonyloxy, ethylaminocarbonyloxy, phenylcarbonyloxy, etc.), cyclic aminocarbonyloxy (e.g. morpholinocarbonyloxy, pyrrolidinocarbonyloxy, piperidinocarbonyloxy, thiomorpholinocarbonyloxy, etc.), trimethylsilyloxy, tert-butyldimethylsilyloxy, and esterified or amidated carboxyl groups as well. As esterified carboxyl groups and amidated carboxyl groups, mention is made of those described above in reference to $R^1$ to $R^5$. While these substituents may be located at optional positions, those located at terminal positions are preferable.

The alicyclic hydrocarbon group may be saturated or unsaturated, which is exemplified by a cycloalkyl group, cycloalkenyl group, cycloalkadienyl group, etc.

Examples of the cycloalkyl group include $C_3$–$C_{10}$ ones such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2-]nonyl, bicyclo[3.3.1]nonyl, bicyclo[4.2.1]nonyl, and bicyclo[4.3.1]decyl.

Examples of the cycloalkenyl group include $C_3$–$C_6$ ones such as 2-cyclopenten-1-yl, 3-cyclopenten-1-yl, 2-cyclohexen-1-yl and 3-cyclohexen-1-yl.

Examples of the cycloalkadienyl group include $C_5$–$C_7$ ones such as 2,4-cyclopentadien-1-yl, 2,4-cyclohexadien-1-yl, and 2,5-cyclohexadien-yl.

As aromatic hydrocarbon groups, mention is made of those shown by Q, and they have substituents likewise.

The aromatic aliphatic hydrocarbon group means an alkyl group having the above-mentioned aromatic hydrocarbon group as substituent. Said aromatic hydrocarbon group may have substantially the same substituents as in the above-mentioned aromatic hydrocarbon group. Said alkyl group is exemplified by $C_1$–$C_4$ alkyl groups such as methyl, ethyl and propyl.

As the aromatic aliphatic hydrocarbon group, mention is made of, for example, benzyl, phenethyl, 3-phenylpropyl, (1-naphthyl)methyl and (2-naphthyl)methyl, preferably benzyl and phenethyl.

This aromatic aliphatic hydrocarbon group may have a substituent on an optional position of its aromatic ring. As the substituent, mention is made of those described in reference to the above-mentioned aromatic hydrocarbon.

The compounds represented by the general formula (II), are those in which Q and R are different from each other.

The above-mentioned tri-substituted phosphine is, in general, a compound represented by the general formula $$(R^6)_3P \qquad (IV)$$

(wherein $R^6$ stands for a $C_1$–$C_8$ alkyl group or an optionally substituted phenyl group).

As optionally substituted phenyl group shown by $R^6$, mention is made of, for example, besides unsubstituted phenyl group, 2-methylphenyl, 3-methylphenyl, 4-methylphenyl and 4-methoxyphenyl. Examples of $C_1$–$C_8$ alkyl groups shown by $R^6$ include methyl, ethyl, propyl, butyl, pentyl, hexyl, heptyl and octyl.

The diazodicarboxylate and diazodicarboxamide employed in the present invention are both compounds represented by the general formula $$R^7\text{—CO—N}=\text{N—CO—}R^8 \qquad (V)$$

(wherein $R^7$ and $R^8$ independently stand for a lower alkoxy group, a di-lower alkylamino group or cyclic amino) [hereinafter sometimes simply referred to as Compound (V)].

Examples of the lower alkoxy group shown by $R^7$ and $R^8$ include $C_1$–$C_6$ ones such as methoxy, ethoxy, propoxy, isopropoxy, butoxy, isobutoxy, sec-butoxy, tert-butoxy, pentyloxy, isopentyloxy, neopentyloxy, tert-pentyloxy, 1-ethylpropoxy, hexyloxy, isohexyloxy, 1,1-dimethylbutoxy, 2,2-dimethylbutoxy, 3,3-dimethylbutoxy and 2-ethylbutoxy, preferably $C_1$–$C_3$ ones. These groups may further be substituted, and, as the further substituted lower alkoxy group, mention is made of those in which the substituted lower alkyl moiety is a substituted lower alkyl which is a substituent of the phenol compound (I) described above.

Examples of the di-lower alkyl amino groups shown by $R^7$ and $R^8$ include dimethylamino, diethylamino and diisopropylamino. And, as the cyclic amino group shown by $R^7$ and $R^8$, mention is made of piperidino group, pyrrolidino group and morpholino group.

The reaction in the present invention is conducted by allowing a phenol compound (I) to react with an optically active secondary carbinol compound (II) in the presence of tri-substituted phosphine (IV) and the compound (V).

This reaction is carried out in an inert solvent such as dichloromethane, chloroform, 1,2-dichloroethane, diethylether, tetrahydrofuran, dioxane, dimethoxyethane, benzene, toluene, pentane, hexane, cyclohexane and tert-butanol, or a mixture of them at temperatures ranging from about −30° C. to 70° C., preferably from −20° C. to 40° C. And, the starting phenol compound (I) in this reaction is employed in an excess amount relative to the compound (II) (2–15 times as much mol., preferably 5–10 times as much mol.).

The compound (IV) is employed in an amount of 1 to 2 times, preferably 1 to 1.5 times as much mol. relative to the compound (I). The compound (V) is also employed in an amount of 1 to 2 times, preferably 1 to 1.5 times as much mol. relative to the compound (I)

In this reaction, a phenol compound (I) reacts with an optically active secondary carbinol compound to give an optically active tri-substituted methane compound (III). In this reaction, the carbon bonding to the hydroxyl group of the secondary carbinol bonds to the carbon at ortho- and/or para-position of the phenol compound (I). For example, in the case where a phenol compound represented by the general formula (I- 2), wherein $R^3$ is not hydrogen, is allowed to react with a compound represented by the general formula (II-1), a compound represented by the general formula

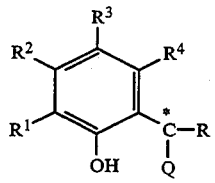

(III-1)

(wherein each symbol is of the same meaning as defined above, provided that $R^3$ is not hydrogen) is obtained. And, in the case where a phenol compound (I), wherein the para-position is unsubstituted and the carbon at the ortho-position is substituted, i.e., a compound (I-1) wherein $R^3$ is hydrogen while $R^1$ and $R^5$ are not hydrogen, is allowed to react with a secondary carbinol, a compound of the general formula

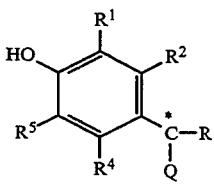

(III-2)

(wherein $R^1$, $R^2$, $R^4$, $R^5$, Q and R are of the same meaning as defined above) is obtained.

In the case where a phenol compound (I) wherein both ortho- and para-positions are unsubstituted is employed, while it reacts with a secondary carbinol compound (II) at both ortho- and para-positions, the reaction at ortho-position occurs prevalently, and, therefore, the resulting tri-substituted methane compound (III) having phenol having hydroxyl group at ortho-position is obtained in an amount more than that having phenol having hydroxyl group at para-position.

In this reaction, the absolute configuration of the resulting compound (III) is reversed relative to that of the compound (II), and the optical purity is substantially maintained.

The object compound (III) thus obtained can be isolated from the reaction mixture by conventional means for isolation and purification, for example, extraction, concentration, filtration, recrystallization, column (or thin-layer) chromatography.

The optically active compound (III) obtained by the present invention, is useful as, for example, an effective ingredient of pharmaceutical composition or an intermediate for producing medicines.

The optically active tri-substituted methane compound (III) obtained by the present invention can be led to optically active compounds of the compounds described in, for example, JPA H2(1990)-152940 by the processes disclosed in these official gazettes.

Examples of the optionally substituted hydroxy group in $R_1$ of the novel phenol derivatives represented by the general formula (A) of the present invention include hydroxy group, a lower alkoxy group having 1 to 4 carbon atoms (e.g., methoxy, ethoxy, propoxy), methoxymethyloxy, benzyloxy, a lower acyloxy group having 1 to 4 carbon atoms (e.g. formyloxy, acetoxy, propionyloxy), tetrahydropyranyloxy and the like.

Examples of the lower alkyl group represented by $R_2$ include alkyl having 1 to 4 carbon atoms such as methyl, ethyl, prophyl, isopropyl, butyl, isobutyl, t-butyl and the like. Examples of the lower alkoxy group, include alkoxy having 1 to 4 carbon atoms such as methoxy, ethoxy, propoxy, isopropoxy, butoxy, isobutoxy, t-butoxy and the like.

Examples of the optionally substituted alkyl group having 1 to 8 carbon atoms represented by $R_3$ and $R_4$ include unsubstituted alkyl groups such as methyl, ethyl, propyl, isopropyl, butyl, isobutyl, t-butyl, pentyl, hexyl, heptyl, octyl and the like as well as these alkyl groups substituted with one or more hydroxy groups, alkoxy groups as defined with respect to $R_2$, halogen atoms (e.g., fluorine, chlorine, bromine) and/or carboxyl groups (e.g., hydroxymethyl, 1-hydroxyethyl, 2-hydroxyethyl, carboxymethyl, 2-carboxyethyl, methoxymethyl, trifluoromethyl, chloromethyl, etc.). Examples of the optionally substituted aralkyl group include one having 7 to 13 carbon atoms such as benzyl, 1-phenylethyl, 2-phenylethyl, diphenylmethyl and the like and these groups may have 1 to 5 substituents, preferably 1 to 3 substituents at any positions thereof. As such substituents, for example, there are halogen atoms such as fluorine, chlorine, bromine and the like. Examples of the halogen atom represented by $R_3$ and $R_4$ include fluorine, chlorine, bromine and the like. As the acyl group having 2 to 7 carbon atoms, there are alkylcarbonyls such as acetyl, propionyl, butyryl, valeryl and the like. As the optionally protected formyl group represented by $R_3$ and $R_4$, n addition to unsubstituted formyl group, there are, for example, 1,3-dioxolan, propylene acetal, 1,3-oxathiolan, dialkyl acetal (the alkyl having 1 to 4 carbon atoms) and the like. As the esterified carboxyl group represented by $R_3$ and $R_4$, there are lower alkoxycarbonyl having 2 to 5 carbon atoms (e.g., methoxycarbonyl, ethoxycarbonyl, etc.), aralkyloxycarbonyl having 8 to 10 carbon atoms (e.g., benzyloxycarbonyl, etc.) and aryloxycarbonyl having 7 to 10 carbon atoms (e.g., phenoxycarbonyl, 4-methylphenyloxycarbonyl, 4-methoxyphenyloxycarbonyl, etc.). As the amidated carbonyl group represented by $R_3$ and $R_4$, in addition to unsubstituted aminocarbonyl, there are substituted aminocarbonyl in which the amino group is substituted with hydroxyl or alkyl having 1 to 4 carbon atoms (e.g., methylaminocarbonyl, ethylaminocarbonyl, i-propylaminocarbonyl, dimethylaminocarbonyl, hydroxyaminocarbonyl, etc.) and cyclic aminocarbonyl (e.g., morpholinocarbonyl, piperidinocarbonyl, pyrrolidinocarbonyl, piperazinocarbonyl, thiomorpholinocarbonyl, etc.). The cyclic aminocarbonyl may have alkyl having 1 to 2 carbon atoms or alkoxy having 1 to 2 carbon atoms at an optional position on the ring.

Examples of the lower alkyl group represented by $R_5$ and $R_6$ include those as defined with respect to the above $R_2$. And, as the lower acyl group represented by $R_6$, there are ones having 2 to 6 carbon atoms such as acetyl, propionyl, butyryl and the like.

Examples of the lower alkoxy group represented by $R_7$ include ones having 1 to 8 carbon atoms such as methoxy, ethoxy, propoxy, i-propoxy, butoxy, pentyloxy, hexyloxy, octyloxy and the like, And, as the lower alkenyloxy group, for example, there are ones having 2 to 6 carbon atoms such as ethenyloxy, 1-propenyloxy, 2-propenyloxy, 1-butenyloxy, 2-butenyloxy and the like.

Examples of halogen atoms as the substituents of phenyl represented by X include those ad defined with respect to the above $R_3$. Examples of the lower alkyl groups as the substituents fo phenyl represented by X include those as defined with respect to the above $R_2$. Examples of the lower alkoxy groups as the substituents of phenyl represented by X include those as defined with respect to $R_2$.

Hydroxymethyl group represented by Y may be substituted and, in addition to unsubstituted hydroxmethyl group, examples thereof include methoxymethyl, acetoxymethyl, 2-tetrahydropyranyloxymethyl, benzyloxymethyl, nitroxy, aminocarbonyloxymethyl, substituted aminocarbonyloxmethyl (e.g., methylaminocarbonyloxymethyl, ethylaminocarbonyloxymethyl, dimethylaminocarbonyloxymethyl, phenylaminocarbonyloxymethyl, etc.), cyclic aminocarbonyloxymethyl (e.g., morpholinocarbonyloxymethyl, piperazinocarbonyloxymethyl, pyrrolidinocarbonyloxymethyl, piperidinocarbonyloxymethyl, thiomorpholinocarbonyloxymethyl, etc.), t-butyldimethylsilyloxymethyl and the like. As the esterified carboxyl group, for example, there are lower alkoxycarbonyl having 2 to 4 carbon atoms such as methoxycarbonyl, ethoxycarbonyl and the like. The amidated carboxyl group represented by Y may be a substituted aminocarbonyl in which the amino group is substituted, or may be cyclic aminocarbonyl. As the substituent of the amino group of the substituted aminocarbonyl, for example, there are alkyl having 1 to 4 carbon atoms such as methyl, ethyl, propyl, isopropyl, butyl and the like, aryl having 6 to 10 carbon atoms such as phenyl, naphthyl and the like (they may further have one or more substituents such as hydroxy, amino, nitro, halogen, methyl, methoxy, etc. at optional positions), hydroxy and the like. Specific examples of the amidated carboxyl group include aminocarbonyl; mono- or dialkylamino-(e.g., methylamino-, ethylamino-, isopropylamino-, dimethylamino-)carbonyl; aralkylamino-[e-g., benzylamino-, αphenethylamino-, β-phenethylamino-, 1-(α-naphthyl-)ethylamino-]carbonyl; phenylaminocarbonyl; substituted phenylamino-(e.g., p-hydroxyphenylamino-, p-methoxyphenylamino-, m-chlorophenylamino-, p-bromophenylamino-)carbonyl; diphenylaminocarbonyl; hydroxyaminocarbonyl; N-hydroxy-N-methylaminocarbonyl; N-hydroxy-N-phenylaminocarbonyl; an amino acid residue in which one hydrogen is removed from the corresponding amino acid (e.g., glycine residue, arginine residue, histidine residue, asparagin residue, proline residue, phenylalanine residue, alanine residue, methionine residue, leucine residue)carbonyl; and the like. As the cyclic aminocarbonyl, for example, there are morpholinocarbonyl, piperidinocarbonyl, piperazinocarbonyl, pyrrolidinocarbonyl, thiomorpholinocarbonyl and the like. Y is preferably a carboxyl group which may be esterified, and, most preferably, is carboxyl.

Though the optically active phenol derivatives represented by the general formula (A) include (R)-form and (S)-form, (R)-form is preferable. $R_1$ is preferably hydroxyl.

Among the phenol derivatives represented by the general formula (A), the following compounds are preferable from the view point of their pharmacological activities.

(R)-7-(4-fluorophenyl)-7-(5-hydroxy-6,7-dimethyl-1-oxoindan-4-yl)heptanoic acid.

(R)-7-(4-fluorophenyl)-7-(2-hydroxy-5-hydroxymethyl-3,4,6-trimethylphenyl)heptanoic acid.

(R)-7-(4-fluorophenyl)-7-(3-formyl-6-hydroxy-2,4,5-trimethylphenyl)heptanoic acid.

(R)-7-(3-acetyl-6-hydroxy-2,4,5-trimethylphenyl)-7-(4-fluorophenyl)heptanoic acid.

(R)-7-(4-fluorophenyl)-7-(6-hydroxy-4,7-dimethylindan-5-yl)heptanoic acid.

Among the phenol derivatives represented by the general formula (A) of the present invention, those wherein X is phenyl, 4-methylphenyl, 4-halogenophenyl, 2-thienyl, 3-thienyl, etc., Y is carboxyl and the number of methylene group (n) is 5 to 9 are preferred from the viewpoint of their pharmacological activities.

Among the phenol derivatives represented by the general formula (A), those wherein $R_1$ is hydroxyl, each of $R_2$, $R_3$ and $R_5$ is methyl, $R_4$ is methyl, formyl, hydroxymethyl or acetyl, X is 4-halogenophenyl, n is 5 and Y is carboxyl are preferable; those wherein $R_4$ and $R_5$ combines each other and represent, taken together, a group $—(CH_2)_a$ or $—(CH_2)_b—CO—$ are also preferable; those wherein $R_3$ and $R_4$ combines each other and represent, taken together, a group $—(CH_2)_a$ or $—(CH_2)_b—CO—$ are also preferable; and those wherein $R_4$ is a group $—CH=NR_7$ wherein $R_7$ is methoxy, ethoxy or 2-propenyloxy, are also preferable.

A part of the optically active phenol derivative represented by the general formula (A) of the present invention can be produced by the above method for producing the optically active tri-substituted methane compound (III). A part of the optically active phenol derivative (A) can also be produced by the following method.

The compound of the general formula (A) wherein Y is carbamoyloxymethyl group, N-substituted carbamoyloxymethyl group, hydroxyaminocarbonyl group, N-substituted hydroxyaminocarbonyl group, hydroxymethyl group, carboxyl group, alkoxycarbonyl group, aminocarbonyl group, substituted aminocarbonyl group, cyano group or tetrazolyl group can be produced from the compound wherein Y is hydroxymethyl group, carboxyl group, alkoxycarbonyl group or acyloxymethyl group according to the reactions as shogun in Scheme 1 which themselves are known.

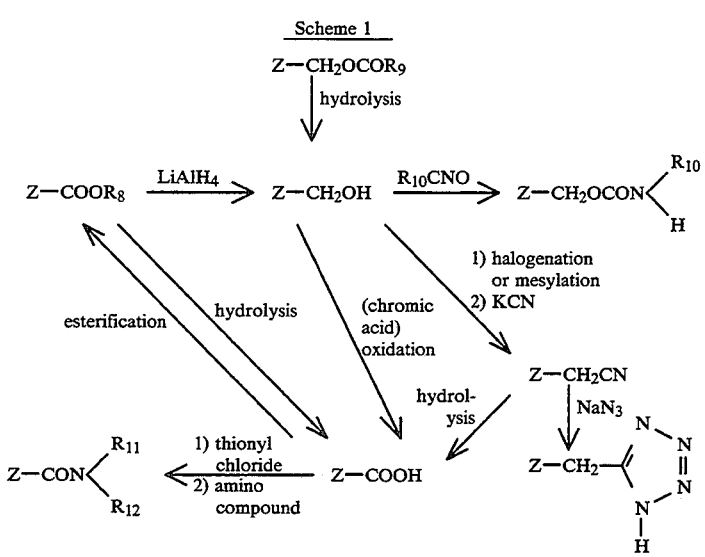

Scheme 1

In Scheme 1, Z is a group represented by the formula:

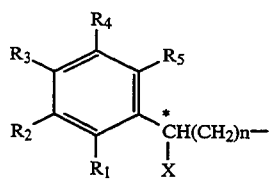

wherein $R_1$, $R_2$, $R_3$, $R_4$, $R_5$, X and n are as defined above; $R_8$ and $R_9$ are alkyl groups having 1 to 3 carbon atoms; $R_{10}$ is hydrogen atom, an alkyl group having 1 to 6 carbon atoms or an aryl group; each of $R_{11}$ and $R_{12}$ is hydrogen atom, a lower alkyl group having 1 to 6 carbon atoms, hydroxy group, a lower alkoxy group having 1 to carbon atoms or an aryl group, provided that at least one of $R_{11}$ and $R_{12}$ is a group other than hydroxy group or an alkoxy group having 1 to 6 carbon atoms; and C means an asymmetric carbon atom.

Further, among the phenol derivatives represented by the general formula (A), those wherein $R_2$ is hydrogen atom, a lower alkyl group or a lower alkoxy group; and $R_3$ is hydrogen atom or a lower alkyl group can also be produced from the corresponding compounds wherein $R_4$ is unsubstituted according to the reactions as shown, in Scheme 2 which themselves are known. Among the phenol derivatives represented by the general formula (A), those wherein $R_4$ and $R_5$ combine with each other to represent a group $—CO—(CH_2)_{a-1}—$ can be prepared by oxidizing the corresponding compounds wherein $R_4$ and $R_5$ combine with each other to represent a group $—(CH_2)_a—$ by using an oxidizing agent such as pyridinium chlorochromate (PCC).

Scheme 2

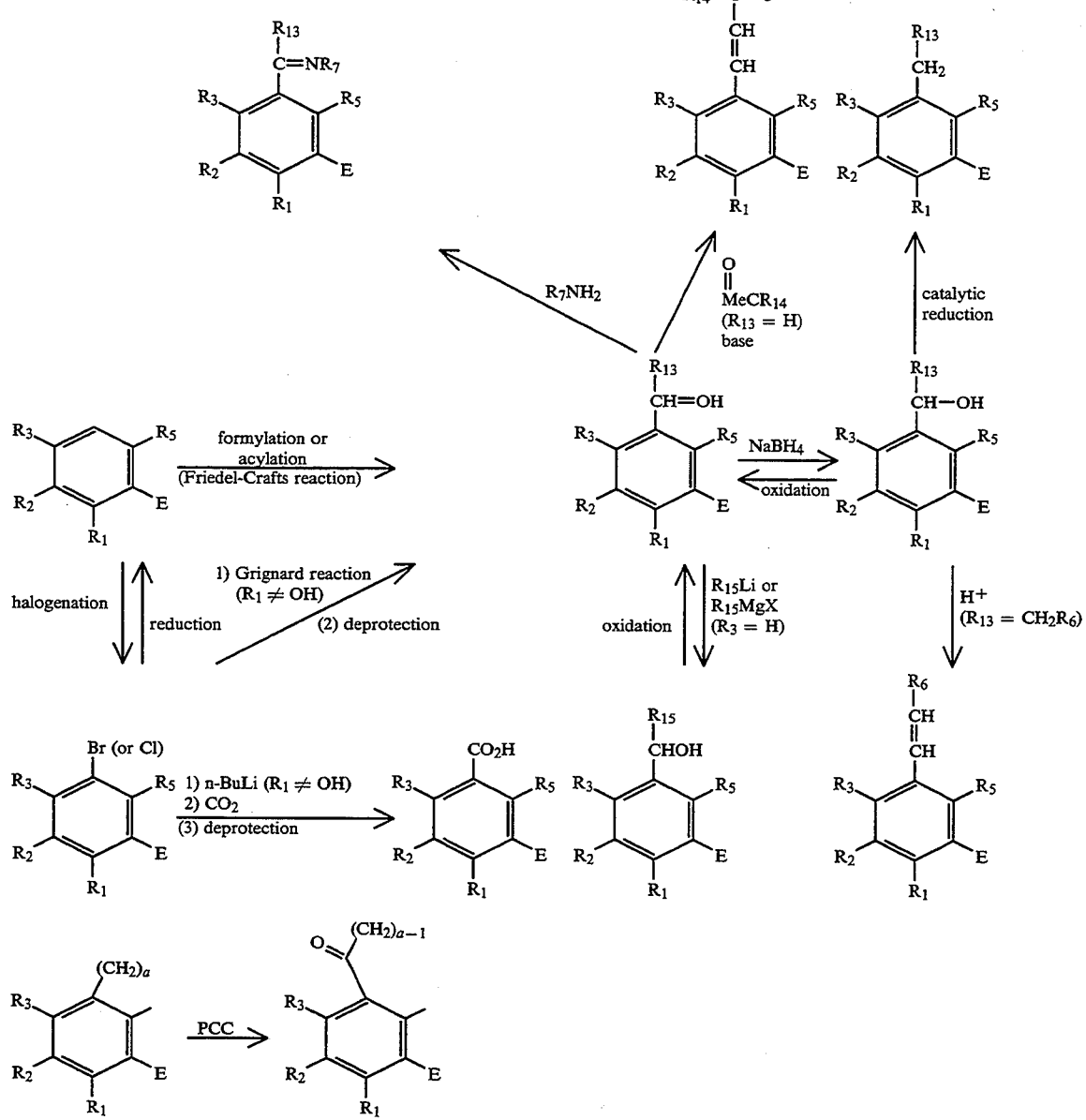

Further, in Scheme 2, when $R_1$ is a protected hydroxy group, the protecting group can be removed by subjecting the resultant to acid hydrolysis or catalytic reduction which itself is known after completion of the reaction to give the optically active phenol derivative represented by the general formula (A). On the other hand, as seen from Scheme 2, the compound represented by the general formula (I) wherein $R_4$ is unsubstituted can be also obtained by reducing the compound wherein $R_4$ is a halogen atom (chlorine or bromine). In Scheme 2, E is

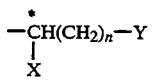

(wherein X, Y, n and $\overset{*}{C}$ are a defined above); $R_{13}$ is hydrogen atom, a lower alkyl group having 1 to 6 carbon atoms, an aryl group or an aralkyl group; $R_{14}$ is a lower alkyl group having 1 to 6 carbon atoms or an aryl group; and $R_{15}$ is a lower alkyl group having 1 to 6 carbon atoms, an aryl group or an aralkyl group.

A compound (A) wherein $R_1$ is a protected hydroxyl group can be obtained from a compound (A) wherein $R_1$ is hydroxyl by a known method, for example, by subjecting a compound (A) wherein $R_l$ is hydroxyl to methylation, methoxymethylation, tetrahydropyranylation, benzylation, acetylation, etc.

Among the optically active phenol derivatives represented by the general formula (A) of the present invention, those wherein Y is free carboxyl group exert antagonistic activities to the receptor of eicosanoides such as thromboxane $A_2$, prostaglandin $H_2$, prostaglandin $D_2$ and the like in an in vitro experimental system. Further, in an in vivo experimental system, even if Y is methyl group, hydroxymethyl group, a substituted hydroxymethyl group, an esterified or amidated carboxyl group or cyano group, in the case that they are converted into carboxyl group by oxidation in the living body (e.g., ω-oxidation, β-oxidation), such phenol derivatives exert antagonistic activites to the receptor of eicosanoids such as thromboxane $A_2$, prostaglandin $H_2$, prostagrandin $D_2$ and the like.

In the living body, thromboxane $A_2$ is mainly biosynthesized from arachidonic acid in platelets or leukocytes through prostaglandin $H_2$. Physioligical activites of thromboxane $A_2$ and prostaglandin $H_2$ are to exert strong platelet aggregation activity and constriction activity against a blood vessel and bronchial smooth muscle in a very low concentration. For example, it has been well known that production of thromboxane $A_2$ is generally accentrated in patients with thronlbosis, myocardial infarction, cerebral infarction, arterial sclerosis, diabetic hypertension, asthma and the like. Accordingly, it is considered that a compound having antagnostic activity to the receptor of thromboxane $A_2$ or prostaglandin $H_2$ can be used as an anti-thrombus agent, anti-vasoconstriction and vasospasm agent, antihypertensive, antiasthmatic or anti-arterial sclerosis agent for treating and preventing various diseases manifested by vasoconstriction, vasospasm, platelet aggregation, thrombus, airway constriction and the like.

Thus, the optically active phenol derivatives of the general formula (A) of the present invention inhibit platelet aggregation caused by arachiodonic acid, collagen, adenosine diphosphoric acid (ADP), platelet activating factor (PAF) and also inhibit pharmacological activities of U-44069 or U-46619 which is a prostaglandin $H_2$ analogue known as a substance for causing platelet aggregation, airway constriction and vasoconstriction through the receptor of thromboxane $A_2$ or prostaglantin $H_2$. Further, they exert improvement of manifestation of arrhythmia and an infarction site in a rat cardiac ischemia-reperfusion model and the like. Furthermore, they exert improvement of the function of rat ischemic kidney and improvement of cerebral ischemia stroke of spontaneous hypertensive rat.

Toxicity of the derivatives of the present invention is low. For example, in case that (R)-7-(4-fluorophenyl)-7-(5-hydroxy-6,7-dimethyl-l-oxoindan-4-yl)heptanoic acid was administered orally to 3 rats at a dose of 1000 mg/kg/day for 2 weeks, no rat died. The derivatives of the present invention can be safely administered orally or parenterally as they are or as pharmaceutical compositions of known forms obtained by admixing them with known pharmaceutically acceptable carriers, excipients and the like, for example, tablets, capsules (including soft capsules and micro-capsules), liquids, injection preparations, suppositories and the like, according to pharmaceutically acceptable methods. The dosage is varied according to patients, routes of administration, conditions of diseases to be treated and the like. However, in the case of oral administration to, for example, an adult patient, usually, a dose per one administration is about 0.1 to 20 mg/kg of the body weight, perferably, about 0.1 to 10 mg/kg of the body weight and, conveniently, the administration is carried out one to two times per day.

Further, since the compound of the present invention has the bulky group on the carbon atom of the alpha position of the side chain, it is hardly inactivated by metabolism in the living body. Thereby, it can maintain the effective blood concentration of the drug for a long period of time and exert superior pharmacological activity with a low dosage.

WORKING EXAMPLES

By the following examples, reference examples and experiments, the present invention will be described in more detail.

Example 1

Preparation of Compound 2

To a solution of 2,3,5-trimethylphenol (13.6 g, 0.10 mol, (S)-3-hydroxy-3-phenylpropylacetate (1.94 g, 10 nunol) and triphenylphosphine (3.90 g, 15.0 nunol) in 1,2-dichloroethane (60 ml) was added dropwise 95% diethyl diazodicarboxylate (DEAD) (2.5 ml) at room temperature. The mixture was stirred for 6 hours at the same temperature range, then the solvent was distilled off under reduced pressure. The residue was subjected to a silica gel column chromatography to obtain 0.94 g of (R)-3-(2-hydroxy-3,4,6-trimethylphenyl)-3-phenylpropyl acetate.

By substantially the same manner as above, Compound 3 was produced. Physico-chemical properties and spectral data of these compounds and those obtained by the following Examples are shown in [Table 1], [Table 2] or [Table 3].

Example 2

Preparation of Compound 9

To a solution of 5-hydroxy-6,7-dimethylindan (0.96 g, 5.9 mmol), methyl (S)-7-(4-fluorophenyl)-7-hydroxyheptanoate (0.30 g, 1.2 mmol) and triphenylphosphine (0.46 g, 1.8 mmol) in 1,2-dichloroethane (15 ml) was added dropwise a solution of 95% diethyldiazodicarboxylate (DEAD) (0.33 ml) in 1,2-dichloroethane (3 ml) at 10° C. taking 30 minutes. The mixture was stirred for one hour at the same temperature range, then the solvent was distilled off under reduced pressure. The residue was subjected to a silica gel coluann chromatography to give 0.18 g of methyl (R)-7-(5-hydroxy-6,7-dimethylindan-4-yl)-7-(4-fluorophenyl)heptanoate. Likewise, Compound 1, 5-8 and 10-17 were prepared.

Example 3

Preparation of Compound 4

To a solution of 2,3,5-trimethylphenol (0.80 g, 5.9 mmol), methyl (S)-7-(4-fluorophenyl)-7-hydroxyheptanoate (0.30 g, 1.2 nunol) and triphenylphosphine (0.46 g, 1.8 mmol) in 1,2-dichloroethane (20 ml) was added at 10° C. a solution of 95% DEAD (0.54 ml) in 1,2-dichloroethane (5 ml) taking 30 minutes. The mixture was stirred for one hour at the same temperature range, then the solvent was distilled off under reduced pressure. The residue was subjected to a silica gel column chromatography to give 0.15 g of methyl (R)-7-(4-fluorophenyl)-7-(2-hydroxy-3,4,6-trimethylphenyl)heptanoate.

Example 4

Preparation of Compound 4

By substantially the same process as in Example 3, using 1,1'-diazodicarbonyldi(piperidine) in place of DEAD, 0.11 g of Compound 4 was obtained.

Example 5

Preparation of Compound 4

By substantially the same process as in Example 3, using diisopropyldiazodicarboxylate (DIAD) in place of DEAD, 0.14 g Compound 4 was obtained.

TABLE 1

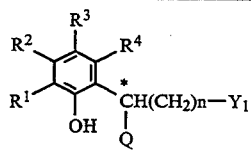

| Compd. No. | $R^1$ | $R^2$ | $R^3$ | $R^4$ | Q | n | $Y_1$ | Steric configuration of starting compd.[2] | Steric configuration Optical purity[2] | Yield (%) | Formula | Physical properties |
|---|---|---|---|---|---|---|---|---|---|---|---|---|
| 1 | Me | Me | H | Me | Ph | 2 | Me | R | S 94.5% ee | 53 | $C_{19}H_{24}O$ | crystal[1] $[\alpha]_D^{28} - 139.6°$ (c = 1, CHCl$_3$) |
| 2 | Me | Me | H | Me | Ph | 2 | OAc | S 98.3% ee | R 98.1% ee | 30 | $C_{20}H_{24}O_3$ | crystal[1] $[\alpha]_D^{28} + 144.4°$ (c = 1, CHCl$_3$) |
| 3 | Me | Me | H | Me | Ph | 2 | OCO—〈 〉—Br | S 98.1% ee | R | 19 | $C_{25}H_{25}BrO_3$ | oil $[\alpha]_D^{28} + 114.5°$ (c = 1, CHCl$_3$) |
| 4 | Me | Me | H | Me | 4-F—Ph | 5 | CO$_2$Me | S 98.0% ee | R 90.5% ee | 34 | $C_{23}H_{29}FO_3$ | crystal[1] |
| 5 | Me | Me | H | Me | 4-F—Ph | 5 | CO$_2$Me | R 96.0% ee | S 89.8% ee | 21 | $C_{23}H_{29}FO_3$ | crystal[1] $[\alpha]_D^{28} - 114.9°$ (c = 0.11, CHCl$_3$), 99.7% ee[3] |
| 6 | Me | Me | Me | Me | 4-F—Ph | 5 | CO$_2$Me | S 98.0% ee | R 92.7% ee | 42 | $C_{24}H_{31}FO_3$ | crystal[1] |
| 7 | Me | —(CH$_2$)$_3$— | | Me | 4-F—Ph | 5 | CO$_2$Me | S 98.0% ee | R 93.3% ee | 42 | $C_{25}H_{31}FO_3$ | oil |
| 8 | —(CH=CH)$_2$— | | H | H | Ph | 2 | OAc | S 98.3% ee | R 91.5% ee | 37 | $C_{21}H_{20}O_3$ | oil |

TABLE 2

| Compd. No. | $R^1$ | $R^2$ | $R^3$ | $R^4$ | Q | n | $Y_1$ | Steric configuration of starting compd.[2] | Steric configuration Optical purity[2] | Yield (%) | Formula | Physical properties |
|---|---|---|---|---|---|---|---|---|---|---|---|---|
| 9 | Me | Me | —(CH$_2$)$_3$— | | 4-F—Ph | 5 | CO$_2$Me | S 98.0% ee | R 93.8% ee | 38 | $C_{24}H_{31}FO_3$ | mp 58–59[3] 99.0% ee[3] $[\alpha]_D^{24} + 104.1°$ (c = 1.00, CHCl$_3$)[3] |
| 10 | Me | Me | Br | Me | Ph | 2 | OAc | S 98.3% ee | R 92.1% ee | 34 | $C_{20}H_{23}BrO_3$ | oil |
| 11 | Me | Me | Br | Me | 4-F—Ph | 5 | COOMe | S 98.0% ee | R | 23 | $C_{23}H_{28}·BrFO_3$ | oil |
| 12 | Me | Me | OMe | Me | 4-F—Ph | 5 | COOMe | S 98.0% ee | R | 29 | $C_{24}H_{31}FO_4$ | oil |

TABLE 2-continued

| Compd. No. | R¹ | R² | R³ | R⁴ | Q | n | Y₁ | Steric configuration of starting compd.[2] | Steric configuration Optical purity[2] | Yield (%) | Formula | Physical properties |
|---|---|---|---|---|---|---|---|---|---|---|---|---|
| 13 | H | Me | Me | Me | Ph | 2 | OAc | S 98.3% ee | R | 47 | $C_{20}H_{24}O_3$ | oil |
| 14 | Me | Me | Ac | Me | 4-F—Ph | 5 | COOMe | S 98.0% ee | R | 24 | $C_{25}H_{31}FO_4$ | oil |
| 15 | Me | Me | —CO(CH₂)₂— | | 4-F—Ph | 5 | COOMe | S 98.0% ee | R | 10 | $C_{25}H_{29}FO_4$ | mp 135–136° C. |
| 16 | Me | Me | H | H | Ph | 2 | OAc | S 98.3% ee | R | 32 | $C_{19}H_{22}O_3$ | oil |
| 17 | Me | Me | —(CH₂)₃— | | 4-F—Ph | 5 | COOMe | R 98.7% ee | S | 33 | $C_{24}H_{31}FO_4$ | mp 59–60° C.[3], >99% ee[3] $[\alpha]_D^{22}$ −104.8° (c = 1.00, CHCl₃)[3] |

[1] Melting point was too low to determine.
[2] Determined by using CHIRAL CEL OJ or CHIRAL CEL OD (both manufactured by Daicel Chemical Industries, Ltd.)
[3] Determined after purification.

TABLE 3

Nuclear Magnetic Resonance Spectra
(solvent CDCl₃, internal standard TMS)

| Compound | |
|---|---|
| 1 | 0.95(t, J=7.2Hz, 3H), 1.10–1.52(m, 2H), 1.79–2.42(m, 2H), 2.02(s, 3H), 2.21(s, 3H), 2.36(s, 3H), 4.41(dd, J=6.1, 9.5Hz, 1H), 4.54(s, 1H), 6.63(s, 1H), 7.15–7.46(m, 5H) |
| 2 | 1.99(s, 3H), 2.00(s, 3H), 2.18(s, 3H), 2.32(s, 3H), 2.40–2.71(m, 2H), 3.84–3.99(m, 1H), 4.04–4.20(m, 1H), 4.54(dd, J=6.4, 9.4Hz, 1H,), 4.63(s, 1H), 6.61(s, 1H), 7.12–7.35(m, 5H) |
| 3 | 2.01(s, 3H), 2.18(s, 3H), 2.32(s, 3H), 2.58–2.86(m, 2H), 4.06–4.45(m, 2H), 4.53(s, 1H), 4.64(dd, J=6.2, 9.4Hz, 1H), 6.61(s, 1H), 7.14–7.39(m, 5H), 7.55(d, J=8.6Hz, 2H), 7.83(d, J=8.6Hz, 2H) |
| 4 | 1.10–1.80(m, 6H), 1.90–2.44(m, 4H), 2.03(s, 3H), 2.21(s, 3H), 2.31(s, 3H), 3.65(s, 3H), 4.33(t, J=7.8Hz, 1H), 4.56(s, 1H), 6.62(s, 1H), 6.94–7.05(m, 2H), 7.23–7.33(m, 2H) |
| 5 | The same as those of Compound 4 |
| 6 | 1.10–1.44(m, 4H), 1.50–1.66(m, 2H), 1.96–2.35(m, 4H), 2.04(s, 3H), 2.10(s, 3H), 2.19(s, 3H), 2.20(s, 3H), 3.65(s, 3H), 4.37(s, 1H), 4.50(t, J=7.5Hz, 1H), 6.88–7.03(m, 2H), 7.18–7.31(m, 2H) |
| 7 | 1.14–1.46(m, 4H), 1.52–1.68(m, 2H), 1.94–2.33(m, 6H), 2.04(s, 3H), 2.22(s, 3H), 2.78–2.90(m, 4H), 3.64(s, 3H), 4.35(s, 1H), 4.38(t, J=8.1Hz, 1H), 6.88–7.01(m, 2H), 7.20–7.32(m, 2H) |
| 8 | 1.98(s, 3H), 2.28–2.59(m, 2H), 3.93–4.18(m, 2H), 4.58(t, J=7.8Hz, 1H), 5.98(s, 1H), 7.10–7.45(m, 9H), 7.68–7.78(m, 1H), 8.02–8.12(m, 1H) |
| 9 | 1.14–1.46(m, 4H), 1.52–1.68(m, 2H), 1.92–2.32(m, 6H), 2.08(s, 3H), 2.16(s, 3H), 2.68–3.03(m, 4H), 3.65(s, 3H), 4.23(t, J=8.3Hz, 1H), 4.40(s, 1H), 6.89–7.02(m, 2H), 7.23–7.35(m, 2H) |
| 10 | 2.03(s, 3H), 2.13(s, 3H), 2.28–2.73(m, 2H), 2.40(s, 3H), 2.51(s, 3H), 3.80–3.96(m, 1H), 4.07–4.22(m, 1H), 4.58(s, 1H), 4.73(dd, J=5.2, 10.2Hz, 1H), 7.17–7.38(m, 5H) |
| 11 | 1.04–1.82(m, 6H), 1.92–2.62(m, 4H), 2.13(s, 3H), 2.40(s, 3H), 2.47(s, 3H), 3.64(s, 3H), 4.53(t, J=8.29, 1H), 4.63(bs, 1H), 6.88–7.60(m, 2H), 7.17–7.30(m, 2H) |
| 12 | 1.15–1.68(m, 6H), 1.97–2.41(m, 4H), 2.04(s, 3H), 2.19(s, 3H), 2.29(s, 3H), 3.64(s, 3H), 3.64(s, 3H), 4.28–4.53(m, 2H), 6.89–7.03(m, 2H), 7.20–7.32(m, 2H) |
| 13 | 2.01(s, 3H), 2.11(s, 3H). 2.20(s, 3H), 2.21(s, 3H), 2.45–2.70(m, 2H), 3.85 4.18(m, 2H), 4.60–4.73(m, 1H), 6.42(s, 1H), 7.09–7.33(m, 5H) |
| 14 | 1.08–1.45(m, 4H), 1.53–1.69(m, 2H), 1.96–2.34(m, 4H), 2.04(s, 3H), 2.11(s, 3H), 2.20(s, 3H), 2.47(s, 3H), 3.65(s, 3H), 4.39(t, J=7.29, 1H), 4.67(s, 1H), 6.91–7.03(m, 2H), 7.18–7.31(m, 2H) |
| 15 | 1.10–1.71(m, 6H), 2.01–2.34(m, 4H), 2.12(s, 3H), 2.62(s, 3H), 2.64(t, J=5.8Hz, 2H), 2.80–3.12(m, 2H), 3.65(s, 3H), 4.31(dd, J=6.0, 9.5Hz, 1H), 5.35(bs, 1H), 6.94–7.07(m, 2H), 7.23–7.34(m, 2H) |
| 16 | 2.02(s, 3H), 2.09(s, 3H), 2.23(s, 3H), 2.24–2.42(m, 2H), 4.05(t, J=6.6Hz, 2H), 4.29(t, J=7.9Hz, 1H), 4.74(s, 1H), 6.75(d, J=8.0Hz, 1H), 6.98(d, J=8.0Hz, 1H), 7.08–7.40(m, 5H) |
| 17 | The same as those of Compound 9 |

Example 6

Preparation of Compound 18

To a solution of methyl (R)-7-(4-fluorophenyl)-7-(2-hydroxy-3,4,6-trimethylphenyl)heptanoate (0.8 g, 2.1 ol) and dichloromethyl methyl ether (0.62 ml) in dichloromethane (10 ml) was added dropwise a solution of titanium tetrachloride (0.76 ml) in dichloromethane (3 ml) under argon atmosphere while maintaining the temperatures of the reaction mixture at a range from −10° C. to −12° C. The reaction mixture was then stirred for 30 minutes at the same temperature range. The reaction mixture was then added to ice-water, which was subjected to extraction with ethyl acetate. The organic layer was washed with water, an aqueous solution of sodium hydrogencarbonate, water and a saturated aqueous saline solution, successively, followed by drying over magnesium sulfate. The solvent was distilled off under reduced pressure. The residue was recrystallized from chloroform/hexane to afford 0.63 g of methyl (R)-7-(4-fluorophenyl)-7-(3-formyl-6-hydroxy-2,4,5-trimethylphenyl)heptanoate. Physico-chemical properties and spectral data of the product were shown in [Table 4].

Example 7

Preparation of Compound 19

To a solution of methyl (R)-7-(4-fluorophenyl)-7-(3-formyl-6-hydroxy-2,4,5-trimethylphenyl)heptanoate (0.55 g, 1.4 mmol) in tetrahydrofuran (6 ml) was added, under argon atmosphere, 1N sodium hydroxide (2.9 ml). The mixture was stirred for 14 hours at room temperature, to which was added 1N hydrochloric acid (2.9 ml), followed by extraction with ethyl acetate. The organic layer was washed with water and a saturated aqueous saline solution, which was dried over magnesium sulfate. The solvent was distilled off under reduced pressure. The residue was recrystallized from acetonitrile to give (R)-7-(4-fluorophenyl)-7-(3-formyl-6-hydroxy-2,4,5-trimethylphenyl)heptanoic acid (0.49 g). Physico-chemical properties and spectral data of this product were shown in [Table 4]. Likewise, Compounds 26, 28, 30 and 31 were prepared.

Example 8

Preparation of Compound 20

To a solution of (R)-7-(4-fluorophenyl)-7-(3-formyl-6-hydroxy-2,4,5-trimethylphenyl)heptanoic acid (0.43 g, 1.1 mmol) in tetrahydrofuran (7 ml) was added, under ice-cooling, sodium borohydride (21.0 mg). The mixture was stirred for two hours at room temperature, to which was added acetone, then the solvent was distilled off under reduced pressure. The residue was neutralized with 1N HCl, which was subjected to extraction with ethyl acetate. The organic layer was washed with water and a saturated aqueous saline solution, followed by drying over magnesium sulfate. The solvent was distilled off under reduced pressure to leave 0.38 g of (R)-7-(4-fluorophenyl)-7-(2-hydroxy-5-hydroxylmethyl-3,4,6-trimethylphenyl)heptanoic acid, whose spectral data are shown in [Table 4].

Example 9

Preparation of Compound 21

To a solution of (R)-3-(2-hydroxy-3,4,6-trimethylphenyl)- 3-phenylpropyl acetate (0.90 g) in acetic acid (10 ml) was added dropwise at room temperature a solution of bromine (0.15 ml) in acetic acid (2 ml). The mixture was stirred at the same temperature for 30 minutes, to which was added ice. The mixture was subjected to extraction with ethyl acetate. The organic layer was washed with an aqueous solution of sodium hydrogencarbonate, water and a saturated aqueous saline solution, successively, followed by drying over magnesium sulfate. The solvent was distilled off under reduced pressure. The residue was subjected to a silica gel column chromatography to give (R)-3-(3-bromo-6-hydroxy-2,4-5-trimethylphenyl)-3-phenylpropyl acetate (1.05 g) as crystals. Physico-chemical properties and spectral data of the product were shown in [Table 4]. X-ray crystallographic analysis of this compound revealed that the steric configuration of the product is R. The compound prepared is the same as Compound No. 10.

Example 10

Preparation of Compound 22

To a suspension of 60% sodlush hydride (1.1 g, 27.2 mmol, washed three times with hexane) in dimethylformamide (30 ml) was added dropwise a solution of (R)-7-(4-fluorophenyl)-7-(3-formyl-6-hydroxy-2,4,5-trimethylphenyl)heptanoic acid (5.0 g, 12.9 mmol) in dimethylformamide (20 ml) at 0° C. The mixture was stirred at room temperature for 30 minutes. To the reaction mixture was added dropwise methyl iodide (1.7 ml, 3.9 g, 27.2 nunol) at 0° C. The mixture was stirred at room temperature for 1.5 hours, to which ice was added. The reaction mixture was extracted with ethyl acetate. The organic layer was washed with water and a saturated aqueous solution of sodium chloride, in the order mentioned, and dried over magnesium sulfate. The solvent was distilled off under reduced pressure, and the residue was subjected to a silica gel column chromatography to give methyl (R)-7-(4-flurophenyl)-7-(3-formyl-6-methoxy-2,4,5-trimethylphenyl)heptanoate (4.6 g). Physico-chemical properties and spectral data of this product are shown in [Table 5].

Example 11

Preparation of Compound 23

To a solution of methylmagnesium bromide in tetrahydrofuran (1 M, 54.3 ml) was added anhydrous tetrahydrofuran (90 ml). To the solution was added dropwise a solution of methyl (R)-7-(4-fluorophenyl)-7-(3-formyl-6-methoxy-2,4,5-trimethylphenyl)heptanoate (4.5 g, 10.9 mmol) in tetrahydrofuran (20 ml) at −78° C., followed by stirring for 30 minutes at the same temperature. To the reaction mixture, an aqueous solution of potassium hydrogensulfate, followed by subjected to extraction with ethyl acetate. The organic layer was washed with water, an aqueous solution of sodium hydrogencarbonate and water, in the order mentioned, and dried over magnesiumsulfate. The organic layer was distilled off under reduced pressure, and the residue was subjected to a silica gel column chromatography to give methyl (R)-7-(4-fluorophenyl)-7-[3-(1-hydroxyethyl)-6-methoxy-2,4,5-trimethylphenyl]heptanoate (4.4 g). Physico-chemical properties and spectral data of this compound are shown in [Table 5].

Example 12

Preparation of Compound 24

A solution of methyl (R)-7-(4-fluorophenyl)-7-[3-(1-hydroxyethyl)-6-methoxy-2,4,5-trimethylphenyl]heptanoate (4.1 g, 9.5 mmol) in dichloromethane (10 ml) was added to a solution of pyridinium chlorochromate (3.3 g, 15.2 mmol) in dichloromethane (20 ml) at room temperature. The mixture was stirred for 2 hours at the same temperature. To the mixture was added diethyl ether. Insolubles were filtered off, and the liltrate was concentrated under reduced pressure. The residue was subjected to a silica gel column chromatography to give methyl (R)-7-(3-acetyl-6-methoxy-2,4,5-trimethylphenyl)-7-(4-fluorophenyl)heptanoate (3.9 g). Physico-chemical properties and spectral data are shown in [Table 5].

Example 13

Preparation of Compound 25

A solution of methyl (R)-7-(3-acetyl-6-methoxy-2,4,5-trimethylphenyl)-7-(4-fluorophenyl)heptanoate (2.0 g, 4.7 mmol) in dichloromethane (10 ml) was added dropwise to boron tribromide (2.0 ml, 5.3 g, 21.0 mmol) in dichloromethane (30 mi) at −78° C. The temperature of the reaction solution was elevated gradually to room temperature, and the reaction solution was stirred for 6 hours at the same temperature. To the reaction solution was was added ice-water at 0° C., and the mixture was extracted with ethyl acetate. The organic layer was washed with water, a saturated aqueous solution of sodium chloride in the order mentioned, and dried over magnesium sulfate. The solvent was distilled off under reduced pressure and the residue was subjected to a silica gel column chromatography to give (R)-7-(3-acetyl-6-hydroxy-2,4,5-trimethylphenyl)-7-(4-fluorophenyl)heptanoic acid (1.56 g). Physico-chemical properties and spectral data are shown in [Table 5].

Example 14

Preparation of Compound 27

To a solution of methyl (R)-7-(4-fluorophenyl)-7-(5-hydroxy-6,7-dimethylindan-4-yl)heptanoate (16.0 g, 40.2 mmol) in toluene (640 ml) was added a mixture of pyridinium chlorochromate (43.3 g, 0.20 ml) and Celite (52 g) at 0° C. under argon atmosphere, followed by stirring for 23 hours at the same temperature. Insolubles were filtered and washed with toluene. The filtrate and washes were combined and concentrated. The residue was subjected to a silica gel column chromatography to give methyl (R)-7-(4-fluorophenyl)-7-( 5-hydroxy-6,7-dimethyl-1-oxoindan-4-yl)heptanoate (10.9 g). The compound obtained is the same as Compound No. 15. Likewise, Compound 29 was prepared. Physico-chemical properties and spectral data are shown in [Table 6].

Reference Example 1

Preparation of Compound 1-1

To a solution of (R)-3,3-diphenyl-1-methyltetrahydro-1H,3H-pyrrolo[1,2-c][1,3,2]oxazaborole (1.1 g) in tetrahydrofuran (20 ml) was added at 0° C. 1M tetrahydrofuran solution of boranetetrahydrofuran complex (4 ml). To this solution were added dropwise a solution of methyl 7-(4-fluorophenyl)-7-oxoheptanoate (10.0 g, 39.6 mmol) in tetrahydrofuran (20 ml) and 1M tetrahydrofuran solution of boranetetrahydrofuran complex (20 ml), simultaneously, taking 25 minutes. The mixture was stirred for 30 minutes at the same temperature range, to which was added methanol (20 ml), followed by stirring for 30 minutes at room temperature. The solvent was distilled off under reduced pressure, and the residue was subjected to a silica gel column chromatography to give methyl (S)-7-(4-fluorophenyl)-7-hydroxyheptanoate (9.91 g). Physico-chemical properties and spectral data of this product are shown in [Table 7]. Likewise, Compound 1-2 was prepared.

Reference Example 2

Preparation of Compound 1-3

To a solution of (S)-1-phenyl-1,3-propanediol (8.0 g, 52.6 mmol) in dichloromethane (80 ml) were added at 0° C. acetic anhydride (5.5 ml) and pyridine (4.7 ml). The mixture was stirred for 6 hours at the same temperature range and for 1.5 hour at room temperature. The reaction mixture was washed with an aqueous solution of sodium hydrogencarbonate, water and a saturated aqueous saline solution, successively. The solvent was distilled off under reduced pressure. The residue was subjected to a silica gel column chromatography to give 4.8 g of (S)-3-hydroxy-3-phenylpropyl acetate. Physico-chemical properties and spectral data of these products are shown in [Table 7].

Reference Example 3

Preparation of Compound 1-4

To a solution of (S)-1-phenyl-1,3-propanediol (5.0 g, 32.9 nunol) and 4-bromobenzoylchloride (7.3 g, 33.2 nunol) in dichloromethane (30 ml) was added dropwise triethylamine (3.1 ml) at 0° C. The mixture was stirred for 1 hour at room temperature. To the reaction solution was added ice water. The organic layer was washed with water and a saturated aqueous solution of sodium chloride in the order mentioned. The residue was subjected to a silica gel column chromatography to give (S)-3-hydroxy-3-phenylpropyl-4-bromobenzoate (7.9 g)- Physico-chemical properties and spectrual data are shown in Table 7.

TABLE 4

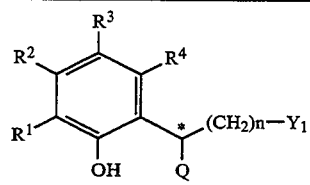

| Compd. No. | R$^1$ | R$^2$ | R$^3$ | R$^4$ | Q | n | Y$_1$ | Steric configuration Optical purity | Formula Properties, m.p. | NMR Spectra (200MHz) TMS internal standard (δ value, ppm), CDCl$_3$ |
|---|---|---|---|---|---|---|---|---|---|---|
| 18 | Me | Me | CHO | Me | 4-F—Ph | 5 | COOMe | R 99.6% ee | C$_{24}$H$_{29}$FO$_4$ [α]$_D^{27}$ + 161.0° (c = 1.035, CHCl$_3$) mp 66–70° C. | 1.06–1.47(m, 4H), 1.52–1.73(m, 2H), 1.96–2.38(m, 4H), 2.10(s, 3H), 2.45(s, 3H), 2.54(s, 3H), 3.65(s, 3H), 4.56(dd, J=6.6, 8.8Hz, 1H), 5.08(s, 1H), 6.95–7.06(m, 2H), 7.19–7.30(m, 2H), 10.58(s, 1H) |
| 19 | Me | Me | CHO | Me | 4-F—Ph | 5 | COOH | R 98.7% ee | C$_{23}$H$_{27}$FO$_4$ [α]$_D^{27}$ + 170.5° (c = 0.51, CHCl$_3$) mp 147–149° C. | *0.96–1.62(m, 6H), 2.00–2.28(m, 4H), 2.10(s, 3H), 2.36(s, 6H), 4.58(bs, 1H), 6.96–7.30(m, 4H), 8.85(s, 1H), 10.44(s, 1H), 11.95(b, 1H) |
| 20 | Me | Me | CH$_2$OH | Me | 4-F—Ph | 5 | COOH | R 99.5% ee | C$_{23}$H$_{29}$FO$_4$ [α]$_D^{20}$ + 72.1° (c = 1.00, DMSO) mp 104° C. (Decomp.) | *0.94–1.54(m, 6H), 1.85–2.44(m, 4H), 2.07(s, 3H), 2.21(s, 6H), 4.20–4.90(m, 4H), 6.94–7.08(m, 2H), 7.13–7.28(m, 2H), 7.82(s, 1H), 11.94(s, 1H) |

TABLE 4-continued

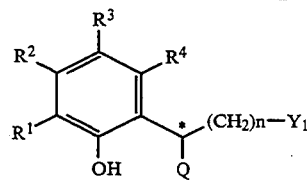

| Compd. No. | R¹ | R² | R³ | R⁴ | Q | n | Y₁ | Steric configuration Optical purity | Formula Properties, m.p. | NMR Spectra (200MHz) TMS internal standard (δ value, ppm), CDCl₃ |
|---|---|---|---|---|---|---|---|---|---|---|
| 21 | Me | Me | Br | Me | Ph | 2 | OAc | R | $C_{20}H_{23}BrO_3$ $[\alpha]_D^{28}$ +182.7° (c = 1.00, CHCl₃) mp 67–68° C. | 2.02(s, 3H), 2.12(s, 3H), 2.28–2.73(m, 2H), 2.40(s, 3H), 2.51(s, 3H), 3.80–3.96(m, 1H), 4.07–4.22(m, 1H), 4.56(s, 1H), 4.73(dd, J=5.2, 10.2Hz, 1H), 7.17–7.38(m, 5H) |

*: DMSO-d₆

TABLE 5

| Compd. No. | R¹ | R² | R³ | R⁴ | Q | n | Y₁ | Steric configuration Optical purity | Formula Properties, m.p. | NMR Spectra (200MHz) TMS internal standard (δ value, ppm), CDCl₃ |
|---|---|---|---|---|---|---|---|---|---|---|
| 22 | \multicolumn{8}{l}{structure: trimethyl, OMe, CHO, (CH₂)₅COOMe, 4-F-phenyl} | R | $C_{25}H_{31}FO_4$ oil $[\alpha]_D^{26}$ +119.7° (c = 1.035, CHCl₃) | 1.04–1.46(m, 4H), 1.52–1.68(m, 2H), 1.87–2.53(m, 4H), 2.21(s, 3H), 2.31(s, 3H), 2.42(s, 3H), 3.31(s, 3H), 3.65(s, 3H), 4.60(t, J=7.7Hz, 1H), 6.87–7.01(m, 2H), 7.09–7.23(m, 2H), 10.58(s, 1H) |
| 23 | \multicolumn{8}{l}{structure: trimethyl, OMe, CH(OH)Me, (CH₂)₅COOMe, 4-F-phenyl} | R | $C_{26}H_{35}FO_4$ oil $[\alpha]_D^{25}$ +97.6° (c = 1.023, CHCl₃) | 1.05–1.46(m, 4H), 1.50–1.77(m, 2H), 1.55(d, J=6.8Hz, 3H), 1.70(s, 1H), 1.91–2.52(m, 4H), 2.18(s, 3H), 2.38(s, 3H), 2.39(s, 3H), 3.31(s, 3H), 3.64(s, 3H), 4.54–4.66(m, 1H), 5.43(q, J=7.0Hz, 1H), 6.84–6.98(m, 2H), 7.09–7.21(m, 2H) |
| 24 | \multicolumn{8}{l}{structure: trimethyl, OMe, COMe, (CH₂)₅COOMe, 4-F-phenyl} | R | $C_{26}H_{33}FO_4$ oil $[\alpha]_D^{26}$ +102.9° (c = 1.02, CHCl₃) | 1.11–1.73(m, 6H), 1.86–2.38(m, 4H), 2.01(s, 3H), 2.11(s, 3H), 2.15(s, 3H), 2.44(s, 3H), 3.27(s, 3H), 3.65(s, 3H), 4.50(t, J=6.6Hz, 1H), 6.86–7.00(m, 2H), 7.21–7.23(m, 2H) |
| 25 | Me | Me | Ac | Me | 4-F—Ph | 5 | COOH | R 99.0% ee | $C_{24}H_{29}FO_4$ $[\alpha]_D^{27}$ +129.1° (c = 1.01, CHCl₃) mp 99–101° C. | 1.14–1.46(m, 4H), 1.53–1.70(m, 2H), 1.96–2.35(m, 4H), 2.04(s, 3H), 2.11(s, 3H), 2.48(s, 3H), 4.39(t, J=7.5Hz, 1H), 4.59(bs, 1H), 6.90–7.04(m, 2H), 7.19–7.31(m, 2H) |
| 26 | Me | —(CH₂)₃— | | Me | 4-F—Ph | 5 | COOH | R 98.1% ee | $C_{24}H_{29}FO_3$ $[\alpha]_D^{27}$ +123.4° (c = 1.01, CHCl₃) | 1.10–1.80(m, 6H), 1.94–2.39(m, 6H), 2.05(s, 3H), 2.23(s, 3H), 2.78–2.93(m, 4H), 3.80–4.90(b, 1H), 4.39(t, J=7.1Hz, 1H), |

TABLE 5-continued

| Compd. No. | R¹ | R² | R³ | R⁴ | Q | n | Y₁ | Steric configuration Optical purity | Formula Properties, m.p. | NMR Spectra (200MHz) TMS internal standard (δ value, ppm), CDCl₃ |
|---|---|---|---|---|---|---|---|---|---|---|
| | | | | | | | | | mp 132–133° C. | 6.90–7.35(m, 2H), 7.21–7.35(m, 2H) |

TABLE 6

| Compd. No. | R¹ | R² | R³ | R⁴ | Q | n | Y₁ | Steric configuration Optical purity | Formula Properties, m.p. | NMR Spectra (200MHz) TMS internal standard (δ value, ppm), CDCl₃ |
|---|---|---|---|---|---|---|---|---|---|---|
| 27 | Me | Me | | —CO(CH₂)₂— | 4-F—Ph | 5 | COOMe | R | $C_{25}H_{29}FO_4$ $[\alpha]_D^{24} + 130.6°$ (c = 1.00, CHCl₃) mp 135–136° C. | 1.10–1.71(m, 6H), 2.01–2.34(m, 4H), 2.12(s, 3H), 2.62(s, 3H), 2.64(t, J=5.8Hz, 2H), 2.80–3.12(m, 2H), 3.65(s, 3H), 4.31(dd, J=6.0, 9.5Hz, 1H), 5.35(bs, 1H), 6.94–7.07(m, 2H), 7.23–7.34(m, 2H) |
| 28 | Me | Me | | —CO(CH₂)₂— | 4-F—Ph | 5 | COOH | R 99.9% ee | $C_{24}H_{27}FO_4$ $[\alpha]_D^{20} + 84.9°$ (c = 0.92, DMSO) 184° C. Decomp. | 1.09–1.84(m, 6H), 2.09–2.36(m, 4H), 2.14(s, 3H), 2.44–3.06(m, 4H), 2.60(s, 3H), 4.35(t, J=7.7Hz, 1H), 6.80(bs, 1H), 6.88–7.02(m, 2H), 7.22–7.35(m, 2H) |
| 29 | Me | Me | | —CO(CH₂)₂— | 4-F—Ph | 5 | COOMe | S | $C_{25}H_{29}FO_4$ $[\alpha]_D + 130.6°$ (c = 1.00, CHCl₃) mp 135–136° C. | same as Compound No. 27 |
| 30 | Me | Me | | —CO(CH₂)₂— | 4-F—Ph | 5 | COOH | S 99.8% ee | $C_{24}H_{27}FO_4$ $[\alpha]_D^{20} - 84.8°$ (c = 0.90, DMSO) mp 184° C. Decomp. | same as Compound No. 28 |
| 31 | Me | Me | | —(CH₂)₃— | 4-F—Ph | 5 | COOH | R 97.2% ee | $C_{24}H_{29}FO_3$ $[\alpha]_D^{20} + 109.7°$ (c = 0.97, CHCl₃) mp 132—133° C. | 1.15–1.47(m, 4H), 1.47–1.70(m, 2H), 1.82–2.21(m, 4H), 2.07(s, 3H), 2.15(s, 3H), 2.31(t, J=7.3Hz, 1H), 2.71–3.03(m, 2H), 2.79(t, J=7.3Hz, 2H), 4.21(t, J=7.9Hz, 1H), 3.9–4.8 (b, 1H), 6.89–7.03(m, 2H), 7.22–7.35(m, 2H) |

TABLE 7

| Compd. No. | X | n | Y₁ | Steric configuration Optical purity | Formula Properties, m.p. | NMR Spectra (200MHz) TMS internal standard (δ value, ppm), CDCl₃ |
|---|---|---|---|---|---|---|
| 1-1 | F | 5 | COOMe | S 98.0% ee | $C_{14}H_{19}FO_3$ oil | 1.17–1.98(m, 9H), 2.29(t, J=7.4Hz, 2H), 3.65(s, 3H), 4.65(t, J=6.7Hz, 1H), 6.96–7.08(m, 2H), 7.26–7.36(m, 2H) |
| 1-2 | F | 5 | COOMe | R 96.0% ee | $C_{14}H_{19}FO_3$ oil | 1.17–1.98(m, 9H), 2.29(t, J=7.4Hz, 2H), 3.65(s, 3H), 4.65(t, J=6.7Hz, 1H), 6.96–7.08(m, 2H), 7.26–7.36(m, 2H) |
| 1-3 | H | 2 | OAc | S 98.3% ee | $C_{11}H_{14}O_3$ oil | 1.95–2.17(2H), 2.05(s, 3H), 2.34(s, 3H), 4.05–4.20(m, 1H), 4.28–4.42(m, 1H), 4.80(t, J=6.6Hz, 1H), 7.25–7.40(m, 5H) |
| 1-4 | H | 2 | OCO—⟨⟩—Br | S 98.1% ee | $C_{16}H_{15}BrO_3$ mp 44–45° C. | 2.06–2.36(m, 2H), 4.33–4.48(m, 1H), 4.51–4.66(m, 1H), 4.88(t, J=6.6Hz, 1H), 7.23–7.50(m, 5H), 7.58(d, J=8.1Hz, 2H), 7.85(d, J=8.1Hz, 2H) |

Experiment 1

Thromboxane A₂ antagonistic activity Effect on thromboxane A₂ minic (U-46619) - induced aggregation in guinea-pig platelets.

Method: Blood was collected in 3.15% sodium citrate (0.1 ml for 0.9 ml of blood) by aortic puncture from anesthetized guinea-pigs. Citrated blood samples were centrifuged at 950 rpm for 10 minutes and 2,000 rpm for 10 minutes at room temperature to obtain platelet-rich plasma (PRP) and platelet-poor plasma (PPP), respectively. The platelet count of PRP was adjusted to 5,000,000/μl with PPP. Platelet aggregation was measured with a photometer (Hematracer 6, Niko Bioscience, Japan). PRP (250 μl) was preincubated at 37° C. for 2 minutes and then incubated for 2 minutes with drug solution (25 μl), followed by stimulation with U-46619 (25 μl). Effect of drug was shown as the percent inhibition of maximal aggregation of drug-treated group versus that of control group. The concentration of U-46619 was chosen to obtain submaximal aggregation in each PRP ($3 \times 10^{-7}$M).

Result: Results shown in Table 8 are % inhibition.

TABLE 8

| Compound No. | % Inhibition of aggregation | | | |
|---|---|---|---|---|
| | $10^{-8}$M | $3 \times 10^{-8}$M | $10^{-7}$M | $3 \times 10^{-7}$M |
| 28 | 0 | 5 | 36 | 89 |
| 20 | 3 | 12 | 77 | — |

Experiment 2

Thromboxane $A_2$ antagonistic activity Effect on thromboxane $A_2$ minic (U-46619) - induced aggregation in human platelets.

Method: Blood was collected in 3.15% sodium citrate (0.1 ml for 0.9 ml of blood) by aortic puncture from anesthetized guinea-pigs. Citrated blood samples were centrifuged at 950 rpm for 10 minutes and 2,000 rpm for 10 minutes at room temperature to obtain platelet-rich plasma (PRP) and platelet-poor plasma (PPP), respectively. The platelet count of PRP was adjusted to 300,000/$\mu$l with PPP. Platelet aggregation was measured with a photometer (Hematracer 6, Niko Bioscience, Japan). PRP (250 $\mu$l) was preincubated at 37° C. for 2 minutes and then incubated for 2 minutes with drug solution (25 $\mu$l), followed by stimulation with U-46619 (25 $\mu$l). Effect of drug was shown as the percent inhibition of maximal aggregation of drug-treated group versus that of control group. The concentration of U-46619 was chosen to obtain submaximal aggregation in each PRP ($10^{-5} \sim 3 \times 10^{-5}$M).

Result: Results shown in Table 9 are % inhibition.

TABLE 9

| Compound No. | % Inhibition of aggregation | | | |
|---|---|---|---|---|
| | $10^{-8}$M | $3 \times 10^{-8}$M | $10^{-7}$M | $3 \times 10^{-7}$M |
| 28 | 13 | 30 | 78 | 100 |
| 20 | — | — | 48 | 100 |

Experiment 3

Inhibitory effect on U-46619 (TXA$_2$ minic) - induced contraction in guinea pig tracheal strip Method: Guinea pig tracheae were removed, and tracheal strips were prepared. Each strip was placed in a 10 ml organ bath containing Tyrode's solution aerated with 5% $CO_2$–95% $O_2$ gas at 37° C. The tracheal strip was placed under resting tension of 1 g. The contractile response of the strip to thromboxane $A_2$ minic U-46619 ($10^{-8}$M) were examined. The strip was treated with the test compound for 1 minute before the addition of U-46619.

Result: The results are shown in Table 10 as the concentration for 50% inhibition (IC$_{50}$).

TABLE 10

| Compound No. | IC$_{50}$ (M) (Concentration for 50% inhibition) |
|---|---|
| 28 | $7.0 \times 10^{-10}$ |

Experiment 4

Inhibitory effect on U-46619 (TXA$_2$ minic) - induced bronchoconstriction in guinea pig.

Method: Six male Hartley guinea pig were used per one group. The guinea pig anesthetized with urethane (1.5 g/kg, i.p.) was fixed in a dorsal position, subjected to tracheotomy and connected to a respirator through a cannula. A side branch of the tracheal cannula was connected to a respirator (Harvard apparatus rodent respirator Type 680) at the rate of 70 strokes/min. and a constant volume of 3 to 5 ml.

Inflation pressure was kept constant at 10 cm $H_2O$.

After treatment with gallamine triethiodide (1 mg/kg, i.v.), U-46619 (10 $\mu$g/kg) dissolved in a physiolosical saline solution was given through a carotid cannula and the airway resistance was measured by the overflow technique of Konzett-Rossler method (Konzett, H. and Rössler, R., Naunyn-Schmiedegerg's Arch, Exp. Path. Pharmak., 195, 71–74 (1940)). A test compound was suspended in 5% gum arabic solution and was administered orally 1 hour before the tratment with U-46619.

Results: The results are shown in Table 11.

TABLE 11

| Compound No. | Dose (mg/kg) | % Inhibition |
|---|---|---|
| 28 | 0.31 | 84** |
| 28 | 1.25 | 84** |

**: $p < 0.01$ vs control group

Effects of the Invention

The present invention provides a novel optically active phenol derivatives having a superior pharmacological activity and a novel method of preparing thereof. In the preparation method, the object compounds can be obtained while maintaining the optical activities of the starting materials.

We claim:

1. An optically active phenol derivative represented by the formula

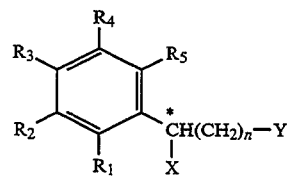

wherein $R_1$ is hydroxyl, alkoxy having 1 to 4 carbon atoms, methoxymethyloxy, benzyloxy, acyloxy having 1 to 4 carbon atoms, or tetrahydropyranyloxy;

$R_2$ is hydrogen, hydroxy, alkyl having 1 to 4 carbon atoms, or alkoxy having 1 to 4 carbon atoms;

$R_3$ is hydrogen, hydroxy, alkyl having 1 to 8 carbon atoms unsubstituted or substituted with hydroxy, alkoxy having 1 to 4 carbon atoms, fluorine, chlorine, bromine, or carboxyl, aralkyl having 7 to 13 carbon atoms unsubstituted or substituted with 1 to 5 halogen atoms selected from the group consisting of fluorine, chlorine and bromine, fluorine, chlorine, bromine, formyl, 1,3-dioxolan, propylene acetal, 1,3-oxathiolan, di($C_{1-4}$)alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, ($C_{1-4}$)alkylaminocarbonyl, morpholinocarbonyl unsubstituted or substituted with ($C_{1-2}$) alkyl or ($C_{1-2}$) alkoxy, piperidinocarbonyl unsubstituted or substituted with ($C_{1-2}$)alkyl or ($C_{1-2}$) alkoxy pyrolidinocarbonyl unsubstituted or substituted with ($C_{1-2}$)alkyl or $(C_{1-2})$alkoxy, piperazinocarbonyl unsubstituted or substituted with $(C_{1-2})$ alkyl or $(C_{1-2})$ alkoxyl —CH=R$_6$ wherein R$_6$ is $(C_{1-4})$alkyl or $(C_{2-6})$ acyl or —CH=N$_7$ wherein R$_7$ is hydroxyl, $(C_{1-8})$alkoxy, $(C_{2-6})$alkenyloxy, or benzhydryloxy;

R$_4$ is alkyl having 1 to 8 carbon atoms unsubstituted or substituted with hydroxy, alkoxy having 1 to 4 carbon atoms, fluorine, chlorine, bromine, or carboxyl, aralkyl having 7 to 13 carbon atoms unsubstituted or substituted with 1 to 5 halogen atoms selected from the group consisting of fluorine, chlorine and bromine, fluorine, chlorine, bromine, formyl, 1,3-dioxolan, propylene acetal, 1,3-oxathiolan, di$(C_{1-4})$alkyl acetal, acyl having 2 to 7 carbon atoms, carboxyl, alkoxycarbonyl having 2 to 5 carbon atoms, aralkyloxycarbonyl having 8 to 10 carbon atoms, aryloxycarbonyl having 7 to 10 carbon atoms, aminocarbonyl, $(C_{1-4})$alkylaminocarbonyl, morpholinocarbonyl unsubstituted or substituted with $(C_{1-2})$ alkyl or $(C_{1-2})$ alkoxy, piperidinocarbonyl unsubstituted or substituted with $(C_{1-2})$alkyl or $(C_{1-2})$ alkoxy, pyrolidinocarbonyl unsubstituted or substituted with $(C_{1-2})$alkyl or $(C_{1-2})$ alkoxy, piperazinocarbonyl unsubstituted or substituted with $(C_{1-2})$alkyl or $(C_{1-2})$ alkoxyl —CH=R$_6$ wherein R$_6$ is $(C_{1-4})$alkyl or $(C_{2-6})$ acyl or —CH=NR$_7$ wherein R$_7$ is hydroxyl, $(C_{1-8})$alkoxy, $(C_{1-2})$alkenyloxy, or benzhydryloxy;

R$_5$ is hydrogen or alkyl having 1 to 4 carbon atoms; or an adjacent two of R$_2$, R$_3$, R$_4$ and R$_5$ may bond to each other to form —(CH$_2$)$_a$— wherein a is 3 or 4, —CH=CH—CH=CH—, —(CH$_2$)$_b$—CO— wherein b is 2 or 3, or —(CH$_2$)$_l$—CO—O— wherein l is 1 or 2;

X is phenyl unsubstituted or substituted with fluorine chlorine bromine, alkyl having 12 to 4 carbon atoms or alkoxy having 1 to 4 carbon atoms at the para-position thereof, or thienyl, Y is methyl, hydroxymethyl, methoxymethyl, acetoxymethyl, 2-tetrahydropyranyloxymethyl, benzyloxymethyl, nitroxymethyl, aminocarbonyloxymethyl unsubstituted or N-substituted with methyl, ethyl, dimethyl, or phenyl, morpholinocarbonyloxymethyl, piperidinocarbonyloxymethyl, pyrolidinocarbonyloxymethyl, piperazinocarbonyloxymethyl, thiomorpholinocarbonyloxymethyl, t-butyldimethylsilyloxymethyl, carboxyl, alkoxycarbonyl having 2 to 4 carbon atoms, aminocarbonyl, mono- or di-$(C_{1-4})$alkylaminocarbonyl, benzylaminocarbonyl, α- or β-phenylethylaminocarbonyl, 1-(α-naphthyl)ethylaminocarbonyl, phenylaminocarbonyl whose benzene ring is unsubstituted or substituted with hydroxyl, amino, nitro, halogen, methyl, or methoxy, diphenylaminocarbonyl, hydroxyaminocarbonyl, N-hydroxy-N-methylaminocarbonyl, N-hydroxy-N-phenylaminocarbonyl, glycine residue-carbonyl, arginine residue-carbonyl, histidine residue-carbonyl, asparagin residue-carbonyl, proline residue-carbonyl, phenylalanine residue-carbonyl, alanine residue-carbonyl, methionine residue-carbonyl, leucine residue-carbonyl, morpholinocarbonyl, piperidinocarbonyl, pyrolidinocarbonyl, thiomorpholinocarbonyl, piperazinocarbonyl, cyano, or tetrazolyl;

n is an integer of 3 to 15, and

C means an asymmetric carbon atom.

2. An optically active compound as claimed in claim 1, wherein the compound is in (R)-form.

3. An optically active compound as claimed in claim 1, wherein the compound is in (S)-form.

4. An optically active compound as claimed in claim 1, wherein n is an integer of 5 to 9.

5. An optically active compound as claimed in claim 1, wherein R$_1$ is hydroxyl.

6. An optically active compound as claimed in claim 1, wherein R$_4$ and R$_5$ combine together and represent a group —(CH$_2$)$_a$— (wherein a is 3 or 4) or a group —(CH$_2$)$_b$—CO— (wherein b is 2 or 3).

7. An optically active compound as claimed in claim 1, wherein R$_3$ and R$_4$ combine together and represent a group —(CH$_2$)$_a$— (wherein a is 3 or 4) or a group —(CH$_2$)$_b$—CO— (wherein b is 2 or 3).

8. An optically active compound as claimed in claim 1, wherein R$_4$ is a group —CH=NR$_7$ (wherein R$_7$ is methoxy, ethoxy or 2-propenyloxy).

9. An optically active compound as claimed in claim 1, wherein the compound is (R)-7-(4-fluorophenyl)-7-(5-hydroxy-6,7-dimethyl-1-oxoindan-4-yl)heptanoic acid.

10. An optically active compound as claimed in claim 1, wherein the compound is (R)-7-(4-fluorophenyl)-7-(2-hydroxy-5-hydroxymethyl-3,4,6-trimethylphenyl)heptanoic acid.

11. An optically active compound as claimed in claim 1, wherein the compound is (R)-7-(4-fluorophenyl)-7-(3-formyl-6-hydroxy-2,4,5-trimethylphenyl)heptanoic acid.

12. An optically active compound as claimed in claim 1, wherein the compound is (R)-7-(3-acetyl-6-hydroxy-2,4,5-trimethylphenyl)-7-(4-fluorophenyl)heptanoic acid.

13. An optically active compound as claimed in claim 1, wherein the compound is (R)-7-(4-fluorophenyl)-7-(6-hydroxy-4,7-dimethylindan-D-yl)heptanoic acid.

14. An optically active compound as claimed in claim 1 wherein

Y is carboxyl, alkoxycarbonyl having 2 to 4 carbon atoms, aminocarbonyl, mono- or di-$(C_{1-4})$alkylaminocarbonyl, benzylaminocarbonyl, α- or β-phenylethylaminocarbonyl, 1-(α-naphthyl)ethylaminocarbonyl, phenylaminocarbonyl whose benzene ring is unsubstituted or substituted with hydroxyl, amino, nitro, halogen, methyl, or methoxy, diphenylaminocarbonyl, hydroxyaminocarbonyl, N-hydroxy-N-methylaminocarbonyl, N-hydroxy-N-phenylaminocarbonyl, glycine residue-carbonyl, arginine residue-carbonyl, histidine residue-carbonyl, asparagin residue-carbonyl, proline residue-carbonyl, phenylalanine residue-carbonyl, alanine residue-carbonyl, methionine residue-carbonyl, leucine residue-carbonyl, morpholinocarbonyl, piperidinocarbonyl, pyrolidinocarbonyl, thiomorpholinocarbonyl, or piperazinocarbonyl.

15. An optically active compound as claimed in claim 1, wherein R$_1$ is hydroxyl; each of R$_2$, R$_3$ and R$_5$ is methyl; R$_4$ is methyl, formyl, hydroxymethyl or acetyl; X is phenyl substituted by fluorine, chlorine, or bromine, at the 4-position; Y is carboxyl and n is 5.

* * * * *